(12) United States Patent
Shafferman et al.

(10) Patent No.: US 8,591,899 B2
(45) Date of Patent: Nov. 26, 2013

(54) **DIAGNOSIS OF *BACILLUS ANTHRACIS* INFECTION BASED ON DETECTION OF BACTERIAL SECRETED BIOMARKERS**

(75) Inventors: Avigdor Shafferman, Nes Ziona (IL); Ofer Cohen, Moshav Neta'im (IL); Theodor Chitlaru, Rehovot (IL); Sagit Sela-Abramovich, Ashkelon (IL); Orit Gat, Rosh Ha'ayin (IL)

(73) Assignee: State of Israel, Represented by Prime Minister's Office, Israel Institute for Biological Research, Nes Ziona (IL)

( * ) Notice: Subject to any disclaimer, the term of this patent is extended or adjusted under 35 U.S.C. 154(b) by 0 days.

(21) Appl. No.: 13/257,304

(22) PCT Filed: Mar. 22, 2010

(86) PCT No.: PCT/IL2010/000234
§ 371 (c)(1),
(2), (4) Date: Sep. 18, 2011

(87) PCT Pub. No.: WO2010/109451
PCT Pub. Date: Sep. 30, 2010

(65) Prior Publication Data
US 2012/0015379 A1    Jan. 19, 2012

(30) Foreign Application Priority Data

Mar. 26, 2009  (IL) .......................................... 197862

(51) Int. Cl.
*A61K 39/40*    (2006.01)
*A61K 39/00*    (2006.01)
*C07K 16/00*    (2006.01)

(52) U.S. Cl.
USPC ................. 424/150.1; 424/139.1; 424/164.1; 530/387.9; 530/388.4; 530/389.5; 435/975

(58) Field of Classification Search
None
See application file for complete search history.

(56) References Cited

U.S. PATENT DOCUMENTS

2003/0138775 A1*  7/2003  Le Page et al. .................. 435/6

OTHER PUBLICATIONS

Kuriyama et al. J. Clin. Microbiol. 27: 285-290, 1989.*
Ahmed, N. et al. (2003) "*An Approach to Remove Albumin for the Proteomic Analysis of Low Abundance Biomarkers in Human Serum*," Proteomics 3:1980-1987.
Altboum, Z. et al. (2002)"*Postexposure Prophylaxis against Anthrax: Evaluation of Various Treatment Regimens in Intranasally Infected Guinea Pigs*," Infect Immun 70:6231-6241.
Antelmann, H. et al. (2005) "*The Extracellular and Cytoplasmic Proteomes of the Non-Virulent Bacillus Anthracis Strain*," Proteomics 5:3684-3695.
Ariel, N. et al. (2002) "*Search for Potential Vaccine Candidate Open Reading Frames in the Bacillus anthracis Virulence Plasmid pXO1:in Silico and InVitro Screening*," Infect. Immun. 7:6817-6827.
Ariel, N. et al. (2003) "*Genome-Based Bioinformatic Selection of Chromosomal Bacillus anthracis Putative Vaccine Candidates Coupled with Proteomic Identification of Surface-Associated Antigens*," Infect. Immun. 71:4563-4579.
Bjorhall, K. et al. (2005) "*Comparison of Different Depletion Strategies for Improved Resolution in Proteomic Analysis of Human Serum Samples*," Proteomics. 5:307-3017.
Bryskier, A. (2002) "*Bacillus anthracis and Antibacterial Agents*," Clinical Microbiology and Infection 8:467-478.
Cendrowski, S. et al. (2004) "*Bacillus anthracis Requires Siderophore Biosynthesis for Growth in Macrophages and Mouse Virulence*," Molec. Microbial. 551:407-417.
Chitlaru, T. et al. (2004) "*Identification of Chromosomally Encoded Membranal Polypeptides of Bacillus Anthracis by a Proteomic Analysis: Prevalence of Proteins Containing S-Layer Homology Domains*," Proteomics 4:677-691.
Chitlaru, T. et al. (2006) "*Differential Proteomic Analysis of the Bacillus anthracis Secretome: Distinct Plasmid and Chromosome CO2-Dependent Cross Talk Mechanisms Modulate Extracellular Proteolytic Activities*," J Bacterial. 188:3551-3571.
Chitlaru, T. et al. (2007) "*Identification of in Vivo-Expressed Immunogenic Proteins by Serological Proteome Analysis of the Bacillus anthracis Secretome*," Infect Immun, 75:2841-2852.
Cohen, S. et al. (2000) "*Attenuated Nontoxinogenic and Nonencapsulated Recombinant Bacillus anthracis Spore Vaccines Protect against Anthrax*," Infect Immun, 68:4549-4558.
Dal Molin, F. et al (2008) "*Ratio of Lethal and Edema Factors in Rabbit Systemic anthrax*," Toxicon, 52:824-828.
Delvecchio, V. G. et al. (2006) "*Proteomic Profiling and Identification of Immunodominant Spore Antigens of Bacillus anthracis, Bacillus cereus, and Bacillus thuringiensis*," Appl Environ. Microbial. 72:6355-6363.
Dinges, M., et al. (2000) "*Exotoxins of Staphylococcus aureus*," Clinical Microbiology Reviews. 13:16-34.
Dixon, T. C. et al. (1999) "*Anthrax*," New Engl J. Med. 341:815-826.
Echan, L.A. et al.(2005) "*Depletion of Multiple High-Abundance Proteins Improves Protein Profiling Capacities of Human Serum and Plasma*," Proteomics 5:3292-3303.
Edwards, K. A. et al. (2006) "*Bacillus anthracis: Toxicology, Epidemiology and Current Rapid-Detection Methods*," Anal. Bioanal. Chem. 384:73-84.
Ewalt, K. et al. (2001) "*Detection of Biological Toxins on an Active Electronic Microchip*," Anal Biochem. 289:162-172.
Francis, A. W. et al. (2005) "*Proteomic Analysis of Bacillus anthracis Sterne Vegetative Cells*," Biochim. Biophyis. Acta 1748:191-200.
Gat, O. et al. (2003) "*Use of a Promoter Trap System in Bacillus anthracis and Bacillus subtilis for the Development of Recombinant Protective Antigen-Based Vaccines*," Infect Immun 71:801-813.
Gat, O. et al. (2005) "*The Solute-Binding Component of a Putative Mn(II) ABC Transporter (Mnta) Is a Novel Bacillus Anthracis Virulence Determinant*," Mol Microbiol 58:533-551.

(Continued)

*Primary Examiner* — S. Devi
(74) *Attorney, Agent, or Firm* — Roach Brown McCarthy & Gruber P.C.; Kevin D. McCarthy

(57) ABSTRACT

A novel and rapid diagnostic method for anthrax infection is provided. Three *B. anthracis* gene products are described, as well as antibodies against the same, which may be used for the detection and monitoring of anthrax infection. Kits for the diagnosis of anthrax are also provided.

9 Claims, 8 Drawing Sheets

(56) References Cited

OTHER PUBLICATIONS

Gat, O. et al. (2006) "*Search for Bacillus anthracis Potential Vaccine Candidates by a Functional Genomic-Serologic Screen*," Infect Immun 74:3987-4001.

Gat, O. et al. (2008) "*Characterization of Bacillus anthracis Iron-Regulated Surface Determinant (Isd) Proteins Containing NEAT Domains*," Mol Microbial. 70:983-999.

Gat, O. et al.( 2007) "*In Vitro Screen of Bioinformatically Selected Bacillus anthracis Vaccine Candidates by Coupled Transcription, Translation, and Immunoprecipitation Analysis*," In: Methods in Molecular Biology vol. 375. In Vitro Transcription and Translation Protocols. Grandi, G. (ed) Humana Press, Totowa, NJ; Chapter 11, pp. 211-233.

Gohar M. et al. (2008) "*The PlcR Virulence Regulon of Bacillus cereus*," PLOS ONE 3(7):e2793. www.plosone.org (pp. 1-9).

Gohar, M. et al. (2002) "*Two-Dimensional Electrophoresis Analysis of the Extracellular Proteome of Bacillus Cereus Reveals the Importance of the PlcR Regulon*," Proteomics 2:784-791.

Gohar, M. et al. (2005) "*A Comparative Study of Bacillus cereus, Bacillus thuringiensis and Bacillus anthracis Extracellular Proteomes*," Proteomics. 5:3696-3711.

Govorukhina, N. I. et al.(2003) "*Sample Preparation of Human Serum for the Analysis of Tumor Markers Comparison of Different Approaches for Albumin and γ-Globulin Depletion*," J. Chromatogr. A. 1009:171-178.

Grosfeld, H. et al. (2003) "*Effective Protective Immunity to Yersinia pestis Infection Conferred by DNA Vaccine Coding for Derivatives of the F1 Capsular Antigen*," Infect. Immun. 71:374-383.

International Preliminary Report on Patentability PCT/IL2010/000234 (2011) pp. 1-10.

Issaq H. et al. (2007) "*Serum and Plasma Proteomics*," Chem. Rev. 107:3601-3620.

Kobiler, et al. (2006) "*Protective Antigen as a Correlative Marker for Anthrax in Animal Models*," Infect. Immun. 74:5871-5876.

Lacy, T. M. et al. (2002) "*Structure and Function of Anthrax Toxin*," Curr. Topics Microbial. Immunol. 271:62-85.

Leppla, S. (1999) "*The Bifactorial B. anthracis Lethal and Oedema Toxins*," In: Comprehensive Sourcebook of Bacterial Protein Toxins. Eds. J.E. Alouf and J.H. Freer. Academic Press. London, UK, pp. 243-263.

Lim, D. et al. (2005) "*Current and Developing Technologies for Monitoring Agents of Bioterrorism and Biowarfare*," Clinical Microbiology Reviews 18:583-607.

Mendelson, I., et al. (2005) "*Efficacious, Nontoxigenic Bacillus anthracis Spore Vaccines Based on Strains Expressing Mutant Variants of Lethal Toxin Components*," Vaccine 23:5688-5697.

Peruski, A.H. et al. (2002) "*Rapid and Sensitive Detection of Biological Warfare Agents Using Time-Resolved Fluorescence Assays*" J. Immunol Methods 263:35-41.

Reuveny, S. et al. (2002) "*Search for Correlates of Protective Immunity Conferred by Anthrax Vaccine*," Infection and Immunity 69:2888-2893.

Righetti, P. G. et al. ( 2006) "*Protein Equalizer™ Technology*:The quest for a democratic proteome*" Proteomics 6:3980-3992.

Rivera V.R. et al. (2006) "*Rapid Detection of Clostridium Botulinum Toxins A, B, E, and F in Clinical Samples, Selected Food Matrices, and Buffer Using Paramagnetic Bead-Based Electrochemiluminescence Detection*," Anal Biochem. 353:248-256.

Rossi, C. A. et al. (2008) "*Identification of a Surrogate Marker for Infection in the African Green Monkey Model of Inhalation Anthrax*," Infect. Immun. 7 6:5790-5801.

Sela-Abramovich, S. et al. (2009) "*Novel and unique diagnostic biomarkers for Bacillus anthracis infection*," Applied and Environmental Microbiol. 75(19):6157-6167.

Shafazand, S. et al. (1999) "*Inhalational Anthrax Epidemiology, Diagnosis, and Management*," Chest. 116:1369-1376.

Stern, E.J. et al. (2008) "Conference Report on Public Health and Clinical Guidelines for Anthrax," Emerg. Infect. Dis. 14:4; http:/ /wwwza.cdc.gov/ EID1contentl141407-0969 .htm; pp. 1-12.

Torres, V.J et al (2007) "*A Staphylococcus aureus Regulatory System Responds to Host Heme and Modulates Virulence*," Cell Host & Microbe 1(2):109-119.

Turnbull, P. C. B. (1999) "*Definitive Identification of Bacillus anthracis—A Review*," J. Applied Microbial. 87:237-240.

Voigt, B. et al. (2004) "*A Proteomic View of Cell Physiology of Bacillus licheniformis*," Proteomics 4:1465-1490.

Voigt, B. et al. (2006) "*The Extracellular Proteome of Bacillus licheniformis Grown in Different Media and Under Different Nutrient Starvation Conditions*," Proteomics 6:268-281.

Voigt, B. et al. (2009) "*Cell Physiology and Protein Secretion of Bacillus licheniformis Compared to Bacillus subtilis*," J. Molec. Microbial. Biotechnol. 16:53-68.

Walz, A. et al. (2007) "*Bacillus anthracia Secretome Time Course Under Host-Simulated Conditions and Identification of Immunogenic Proteins*," Proteome Science 5(1); pp. 1-11.

Wang,Y.Y. et al. (2003) *A Simple Affinity Spin Tube Filter Method for Removing High-Abundant Common Proteins or Enriching Low-Abundant Biomarkers for Serum Proteomic Analysis*, Proteomics 3:243-248.

Wu, H.-J. et al. (2008) "Discovery of Virulence Factors of Pathogenic Bacteria," Current Opinion in Chemical Biology. 12:93-101.

\* cited by examiner

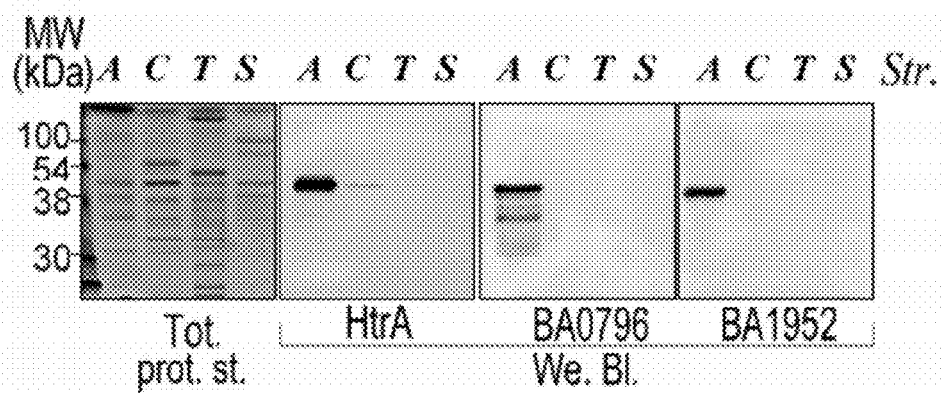
Fig. 4A
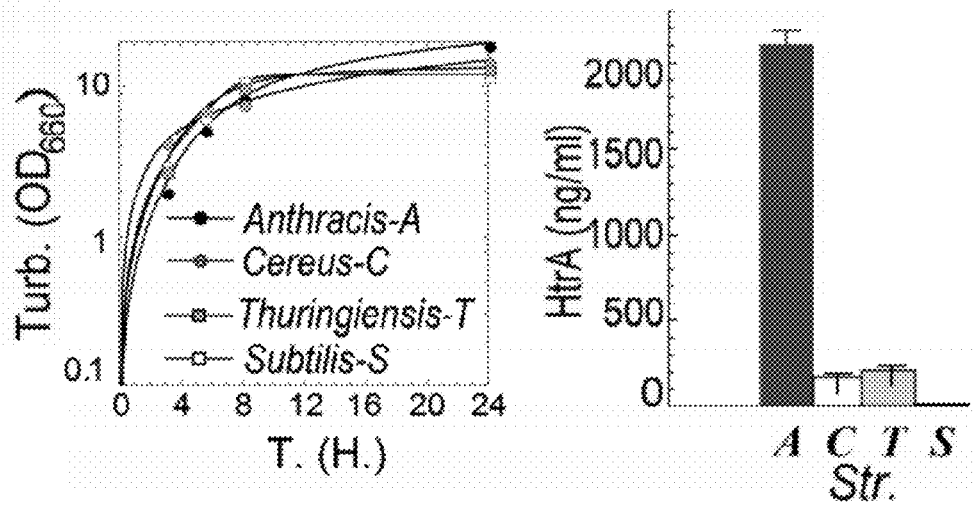
Fig. 4B
Fig. 4C

BA3660(SEQ ID NO:1)

```
  1 mgyydgpnln eehsstrevr ksgskkqyff tglvgavvga vslsfaapym pwagnngatv
 61 ssfssdskve qtvvpvvnka knetdlpgml egakdvvvgv lnmqqsldpf amqptgqeqq
121 agsgsgvlyk kagnkeyivt nnhvvdqank lavklsdgkk vdaklvgkdp wldlavveld
181 ganvrkvatl gdsskirage kaiaignplg fdgsvtegli sskereipvd ldgdkradwn
241 aqvlqtdaai npgnsggalf nqngeiigin sskiaqgsve glgfaipinl akpvieslek
301 dgvvkrpalg vgvvsledvq aya vnqlkvp kevtngvvlq klypispaek agleqydivv
361 aldnckvens lqfrkylyek kkvgekvevt fyrngqkmtk tatladnsat knq
```

BA1952(SEQ ID NO:2)

```
  1 mkkviaglaa asvvgvavpg mdsaqaqvsn ealkeingqa qtgttvtetk tvetksdlky
 61 tvtacvlnvr sgagtghsvi skvkqgqvlq viggengwfk vtvngqtqyv sgdfvttggk
121 tgttvggqtg tytvn vssln vrtgpstsht vlgsvnkgkt vgvvseevgdv fkinfnggtg
181 yvskdfvtkg gsavsnqtqq pttannttv qtggsyvvnt galkvrtgpa tynaviggvt
241 ngtvlnvtga engwykinhn grtghvsadf vkfvkggvnn vtnnvqmpvk dvqkpttggn
301 tssiagfars lngspyrtag ttpagfdcsg fihyvlnqtg hkgarqtvag ywesktktsn
361 pqpqdlvyfq ntyksgpshm gvylngqfi saetdatgvr lssvsnsyws khllgytkay
```

BA0796(SEQ ID NO:3)

```
  1 mkkfmglata avfglglftt sakaetivtt dvlnvrenpt teskvvgkll dgykvnvlht
 61 engwskvkln sgkeafisad ytkdtyyvta nvlnvragan tdseilgklk qgdvletthq
121 vengwigfey ngktayv hvp yltgkapvkv qpvvkaektt tvqdtakava ttkarevaet
181 qakakaeeat karevaeaga aakareaaka qeaakaqaea kaqeaaeaga aakageaaka
241 reaakaqaea kaqeaaeare aakagkpatq qpvaketata apsssrelrv vataytadpl
301 engykagdqv ksalghnlta npnmkliavd psviplgskv wv egygvais gdtggalkgn
361 kidvlmpdkg tasnwgrktv tvkvln
```

Fig. 5

DIAGNOSIS OF *BACILLUS ANTHRACIS* INFECTION BASED ON DETECTION OF BACTERIAL SECRETED BIOMARKERS

CROSS-REFERENCE TO RELATED APPLICATIONS

This application is a 35 U.S.C. §371 National Stage filing of United States Patent Application No. PCT/IL2010/000234 (filed Mar. 22, 2010; Pending), which application claims priority under 35 U.S.C. §119 to Israeli Patent Application No. 197862 (filed on Mar. 26, 2009).

FIELD OF THE INVENTION

The present invention relates to infectious diseases. In particular, the present invention relates to diagnostic methods for identification of anthrax.

BACKGROUND OF THE INVENTION

All publications mentioned throughout this application are fully incorporated herein by reference, including all references cited therein.

The gram-positive spore-forming bacterium *Bacillus anthracis* (*B. anthracis*) is the causative agent of anthrax, a rare fatal disease which is initiated, in its most severe form, by inhalation of infected spores. Due to the severity of the disease, the ease of respiratory infection and the everlasting resistance of the spores to unfavorable environmental conditions, *B. anthracis* is considered a potential biological warfare agent (for review, see Mock and Fouet, 2001), and in recent years the need for novel reliable diagnostic approaches, improved vaccination strategies, novel therapeutic targets and better understanding of the pathogenesis, have been widely acknowledged.

Inhaled *B. anthracis* spores are taken up by alveolar macrophages, germinate into vegetative bacilli which eventually invade the blood stream where they multiply massively and secrete toxins and virulence factors. Anthrax is toxinogenic in the sense that the bacterial binary exotoxin is necessary for the onset of the disease (Lacy and Collier, 2002), yet other factors may be require for the colonization and expansion of the bacteria in the host (for example Cendrowski et al., 2004; Gat et al., 2005). The toxin is composed of three proteins: protective antigen (PA, which mediates binding to the receptor on target cells and internalization of the toxin), lethal factor (LF, a zinc protease targeting MAP kinase) and edema factor (EF, a calmodulin dependent adenylate cyclase; Leppla, 1999). The genes encoding for the three exotoxin components are located on the native pXO1 virulence plasmid. Genes encoding for functions involved in the synthesis of a polyglutamyl immunologically-inert capsule that protects bacteria from phagocytosis are located on a second native virulence plasmid, pXO2 (Leppla, 1999).

In humans, the initial symptoms of anthrax inhalation are nonspecific, reminiscent of influenza-like, upper respiratory track infections. The second stage is characterized by high fever, respiratory failure, dyspnea and shock. Unless promptly treated, death occurs within 24 hours of the onset of the second stage preceded by massive bacteremia (Dixon et al., 1999; Shafazand et al., 2008; Stern et al., 2008). The mandatory treatment for anthrax is based on administration of antibiotics (Stern et al., 2008; Bryskier et al., 2002), yet studies of the disease in animal models have clearly established that the time of antibiotic administration post infection is crucial for the effectiveness of the treatment, strongly supporting the importance of rapid diagnosis (Altboum et al., 2002). As of today, due to the severity of the disease and its rapid progression, treatment is administered in each confirmed contact with contaminated areas (for review, see Stern et al. 2008).

Early accurate diagnosis of anthrax is complicated by the rarity of the disease and the nonspecific nature of the symptoms. Microbiologic identification of anthrax is based on the non-hemolytic nature of the typically white/gray colonies and the rod morphology of the gram positive non-motile bacilli detected in clinical samples or blood cultures (Turnbull, 1999; Edwards et al., 2006; Shafazand et al., 1999). Immunofluorescence and immunohystochemistry targeted to bacterial proteins are not routinely conducted. Later in the course of the disease, seroconversion to the various components of the toxin may serve only as a retrospect confirmation of primordial exposure. With the advent of genetic methodologies, *B. anthracis* is specifically and accurately detected in cultures inoculated with clinical and forensic samples, by PCR usually designed to amplify genes located on the native virulence plasmids (Edwards et al., 2006). The use of PA as a disease biomarker has been suggested owing to the presence of this protein in detectable amounts in the circulation of infected animals (Kobiler et al., 2006; Rossi et al., 2008). EF and LF can be detected in the circulation only at very late stages of the disease, aborting their use as disease biomarkers (Edwards et al., 2006).

In recent years, the search for novel disease biomarkers in general and bacterial infection in particular has exploited the approach of the global biological inspection based on functional genomic or proteomic studies (Wu et al., 2008). The present inventors have documented previously such global surveys combined with serological study of *B. anthracis* for identification of vaccine and diagnostic marker candidates among exposed (secreted or membranal) proteins (Ariel et al., 2002, 2003; Chitlaru et al., 2004, 2006, 2007; Gat et al., 2006).

Therefore, it is an object of the present invention to provide a method for the diagnosis of anthrax, through the specific and rapid detection of biomarkers described by the inventors. In particular, the inventors describe herein a method for diagnosing *B. anthracis* infection through the detection of three secreted proteins, namely the products of locus BA3660, BA1952 and BA0796.

As will be shown by the specification and the following Examples, the diagnostic method of the invention is particularly suitable for detection and monitoring of *B. anthracis* infection. Moreover, the sensitive diagnostic method of the invention may be applied for early detection and diagnosis of anthrax, as well as for monitoring efficiency of therapeutic treatments and delayed confirmation of *B. anthracis* infection.

These and other uses and objects of the invention will become apparent as the description proceeds.

SUMMARY OF THE INVENTION

In their search for bacterial biomarkers following infection with *B. anthracis*, the present inventors identified three secreted proteins, which proved valuable for developing a new method for diagnosis of Anthrax infection, which is described herein.

Thus, in a first aspect, the present invention provides a method for the diagnosis of *Bacillus anthracis* (*B. anthracis*) infection in a sample, said method comprising the steps of:

(a) providing at least one recognition-agent which specifically recognizes a *B. anthracis* bio-marker selected from the group consisting of HtrA (BA3660), NlpC/P60-domain endopeptidase (BA1952), and the protein specified by the BA0796 locus (BA0796), or of any fragment, or derivative thereof;

(b) contacting an aliquot of said sample with at least one recognition-agent of (a) under conditions allowing the interaction of said at least one recognition agent to at least one *B. anthracis* specific bio-marker; and (c) detecting the recognition of said at least one recognition agent to at least one *B. anthracis* specific bio-marker by suitable means and thereby the presence of at least one bio-marker in said sample;

whereby detection of the presence of at least one *B. anthracis* specific bio-marker indicates that said sample is infected with *B. anthracis*.

In one embodiment of said method of the invention, said recognition-agent is an antibody specific for a *B. anthracis* bio-marker selected from the group consisting of BA3660, BA1952, and BA0796, or of any fragment or derivative thereof.

In another embodiment of said method of the invention, said sample is any one of a body fluid and a culture-derived sample.

In a further embodiment of the method of the invention, said suitable means is an immune affinity procedure.

In another further embodiment of the method of the invention, said sample undergoes a step of affinity enrichment of low-abundance proteins before step (b).

In another aspect, the present invention provides a kit for the diagnosis of *B. anthracis* infection, wherein said kit comprises the following components:

(a) at least one recognition-agent which specifically recognizes at least one *B. anthracis* bio-marker selected from the group consisting of BA3660, BA1952, and BA0796, or of any fragment or derivative thereof;

(b) instructions for carrying out the detection of the presence of a *B. anthracis* bio-marker in a sample.

Optionally, the kit provided by the present invention further comprises at least one of:

(a) at least one means for collecting a sample to be tested;

(b) at least one compartment containing at least one recognition-agent which specifically recognizes at least one *B. anthracis* bio-marker selected from the group consisting of BA3660, BA1952, and BA0796, or of any fragment or derivative thereof;

(c) at least one reagent necessary for recognition of at least one of said recognition-agent to at least one of said *B. anthracis* bio-marker;

(d) at least one assay reagent for enabling detection of said recognition indicating the presence of said at least one bio-marker; and (e) at least one control sample.

In particular, said recognition-agent provided with the kit of the invention is an antibody specific for a *B. anthracis* bio-marker selected from the group consisting of BA3660, BA1952, and BA0796, or any fragment or derivative thereof.

In one embodiment of said kit, said sample is any one of a body fluid or a culture-derived sample.

In another embodiment of the kit of the invention, said recognition of said recognition-agent to said *B. anthracis* bio-marker is detected by an immune-affinity procedure.

In a further aspect, the present invention provides the use of an antibody or a fragment thereof, which specifically recognizes and binds a *B. anthracis* bio-marker, in the preparation of a composition for the detection of *B. anthracis* infection in a sample, wherein said bio-marker is one of BA3660, BA1952, and BA0796.

In another further aspect, the present invention provides the use of a *B. anthracis* protein or a fragment thereof in the preparation of a composition for detecting *B. anthracis* infection in a sample, wherein said protein is one of BA3660, BA1952, and BA0796.

In particular, said detection using a *B. anthracis* protein or a fragment thereof is generally at a later stage of infection, following seroconversion.

In a yet further aspect, the present invention provides the use of a *B. anthracis* protein or a fragment thereof as a biomarker for the diagnosis of anthrax in a subject, wherein said protein is one of BA3660, BA1952, and BA0796.

Abbreviations: Ser.=serum; Fl.-th.=Flow-through; En.ser.=Enriched serum; Alb.=Albumin; Tot. prot. st.=Total protein stain; We.=Western; N.-tr. ser.=Non-treated serum; En.ser.=Enriched serum; Hyp.=Hyperimmune; anth.=anthracis; Na.=Naïve; Inf.=Infected; We.Bl.=Western Blot.

Figure 1A:
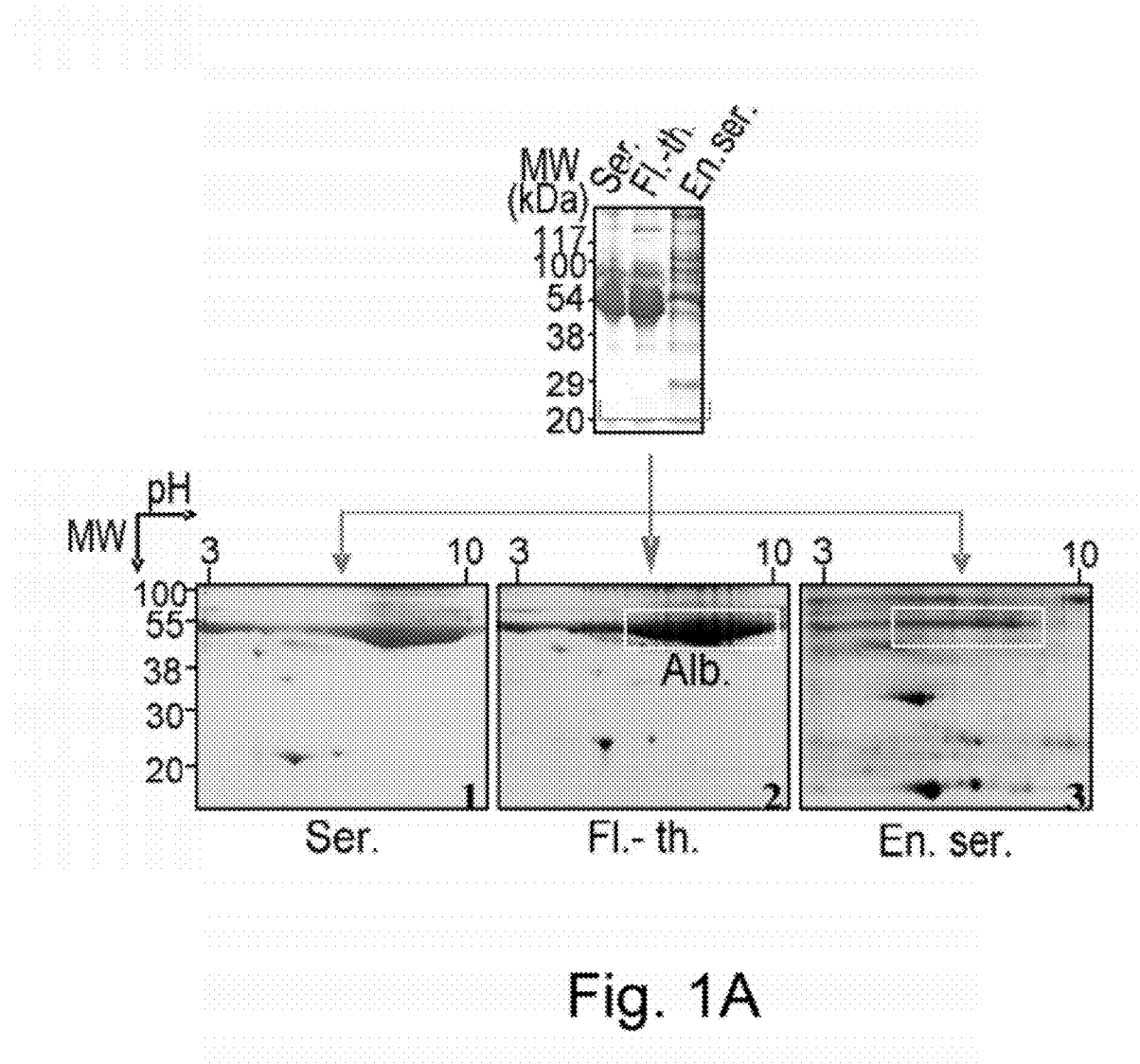
FIGS. 1A-1B: Visualization of scarce serum and/or bacterial proteins following removal of abundant proteins by Proteominer™ affinity depletion.

FIG. 1A: Rabbit serum before ("Serum") and after ("Enriched serum") affinity chromatography, and Flow-through were resolved by one-dimensional (1D)-SDS-PAGE (top) or two-dimensional electrophoresis (2DE) (bottom) gels (marked 1, 3 and 2, respectively) stained by COOMASSIE® blue. Note that the affinity column unbound material (marked "Flow-through") exhibits similar profile to the serum, indicating efficient removal of the abundant proteins. Protein amounts loaded: top gel, serum and flow-through, 200 μg; enriched serum, 20 μg; all 2D gels (bottom), 200 μg.

Figure 1B:
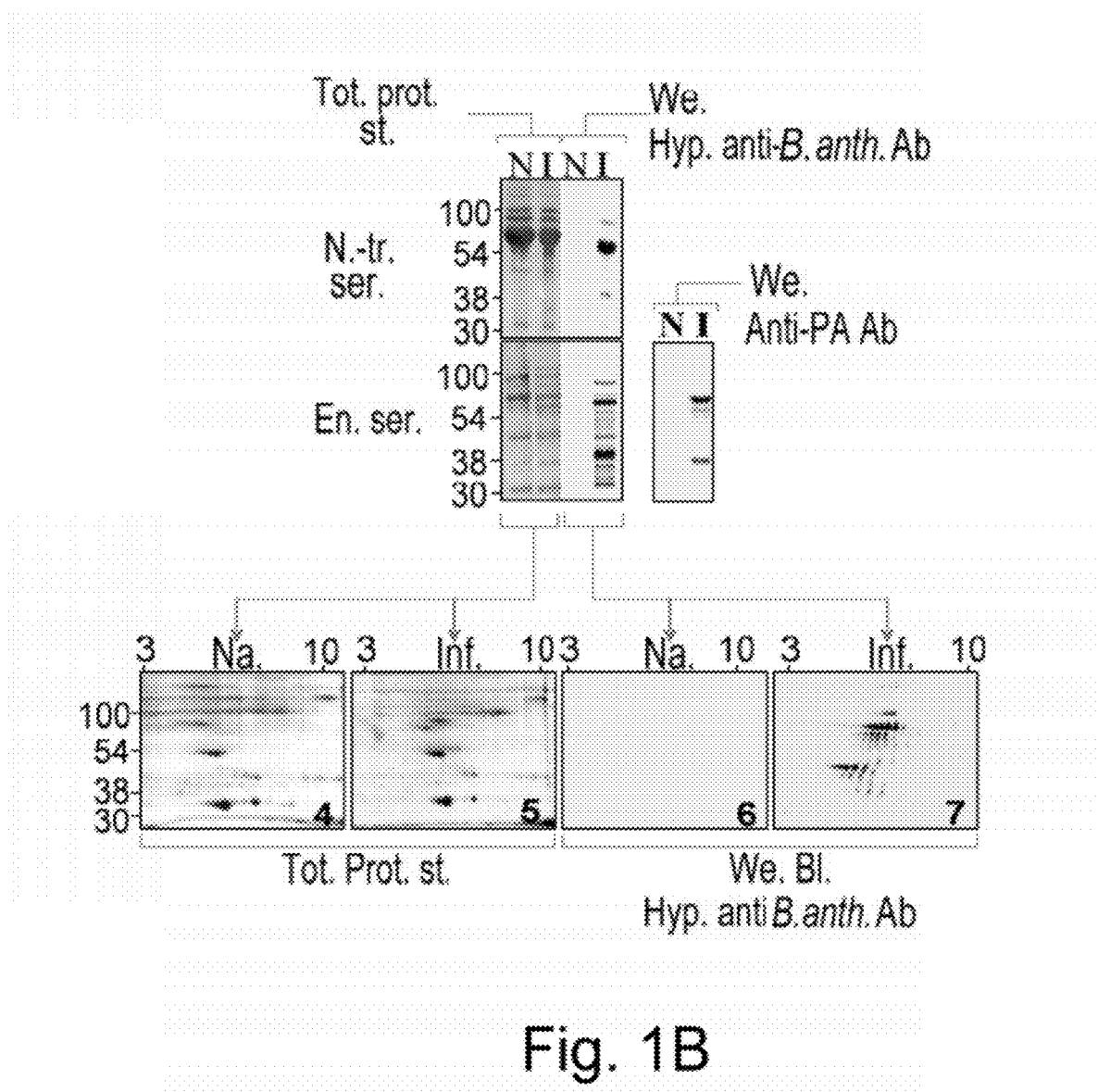

FIG. 1B: Plasma samples derived from naïve (N) or infected (I) rabbits, before ("Non-treated serum", 200 μg) or after removal of abundant proteins ("Enriched serum", 20 μg on 1D-SDS-PAGE gels and 200 μg in the respective 2DE gels) were subjected to 1D-SDS-PAGE (top left) and 2D (bottom gels 4 and 5) SDS-PAGE and Western analysis (top right and bottom gels 6 and 7) probed with anti-*B. anthracis* hyperimmune serum or with specific anti-PA antibodies, as indicated.

FIG. 2A-2D: Detection of HtrA (BA3660), the NlpC/P60-domain endopeptidase (BA1952) and the product of gene BA0796 in bacteremic sera and blood culture using specific antibodies.

Abbreviations: Tot. prot.=Total protein; We.=Western; T. cult.=Time in culture; h=hours; En.ser.=Enriched serum; Hyp.=Hyperimmune; anth.=*anthracis*; Na.=Naïve; Inf.=Infected.

Figure 2A:
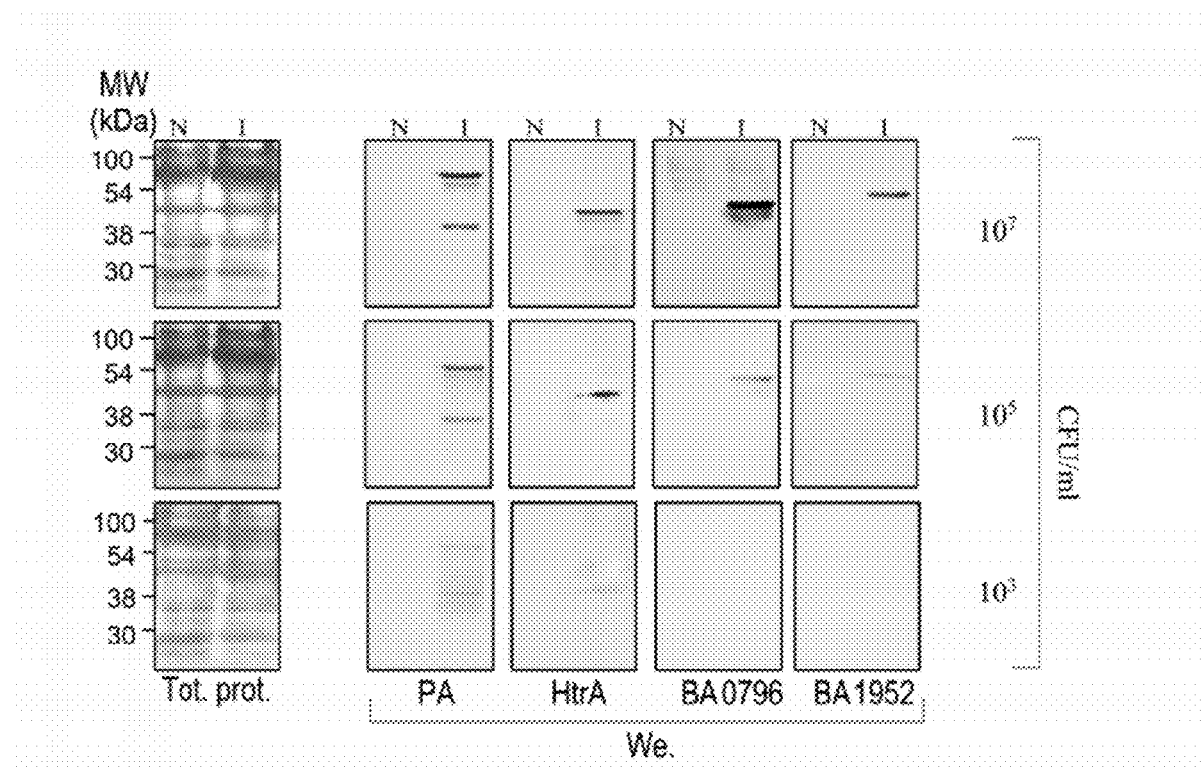

FIG. 2A: 30 μg of sera collected from (N) naïve or (I) infected rabbits ($10^3$-$10^7$ colony forming units [cfu]/ml, as indicated) were subjected to Proteominer™ affinity chromatography for removal of abundant proteins and examined by Western analysis using 1:500 dilutions of the indicated antibodies (generated in mice by DNA vaccination). Western blots were developed by ECL using horseradish peroxidase conjugated goat anti-mouse antibodies. No specific signals could be detected in infected rabbit sera before removal of abundant proteins (not shown).

Figure 2B:
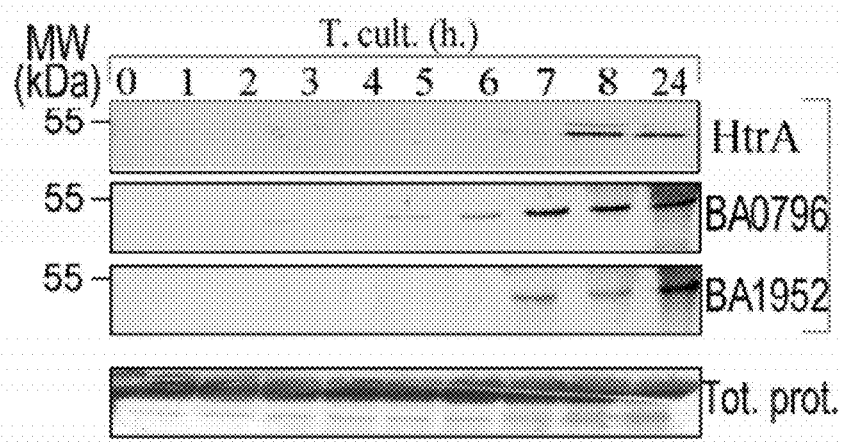

FIG. 2B: Similar analysis using sera of infected animals exhibiting increasing levels of bacteremia, as indicated. Standard (Bactec™+) clinical blood culture flasks were inoculated with 10 ml rabbit blood samples (final volume in flask-25 ml) containing $10^3$ cfu/ml.

Figure 2C:
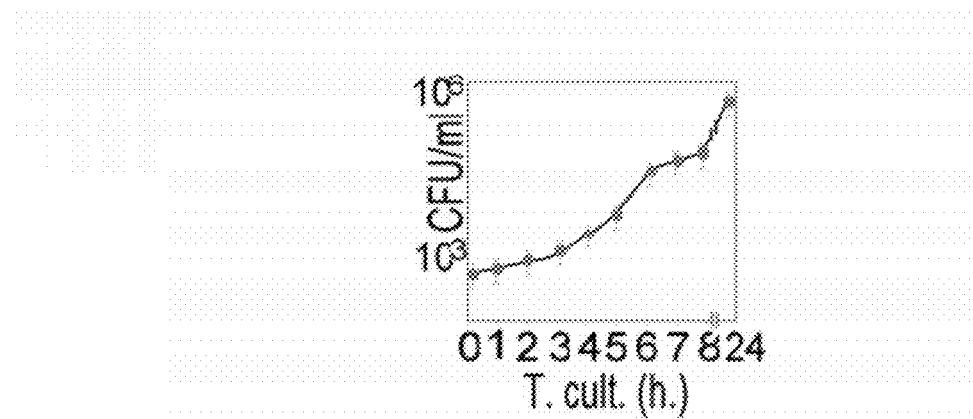

FIG. 2C: Serial dilutions of the 1 ml culture samples collected at the indicated times were plated for calculation of the bacterial growth. 30 µg (protein) of each sample were subjected to SDS-PAGE and Western blot analysis with the indicated specific antibodies, as described in FIG. 2B.

Figure 2D:
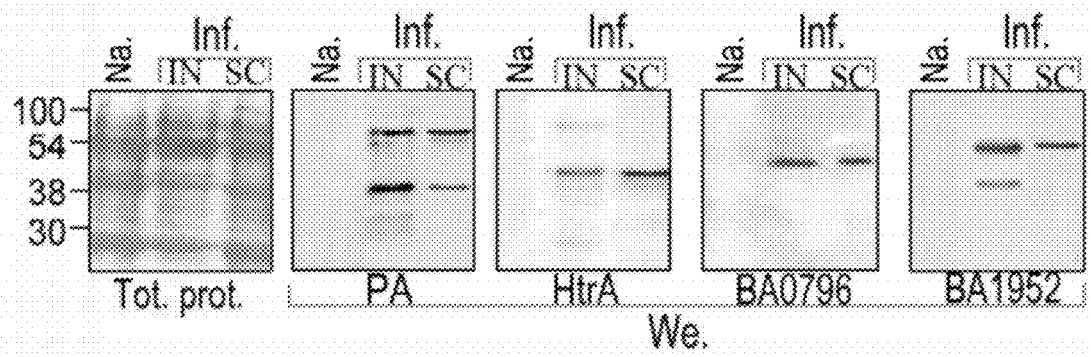

FIG. 2D: SDS-PAGE and Western blot analysis (similar to panel 2A) for immunodetection of the novel biomarkers in sera ($10^7$ cfu/ml) collected from rabbits infected by the intranasal (IN) or subcutaneous (SC) routes of administration.

Figure 3A:
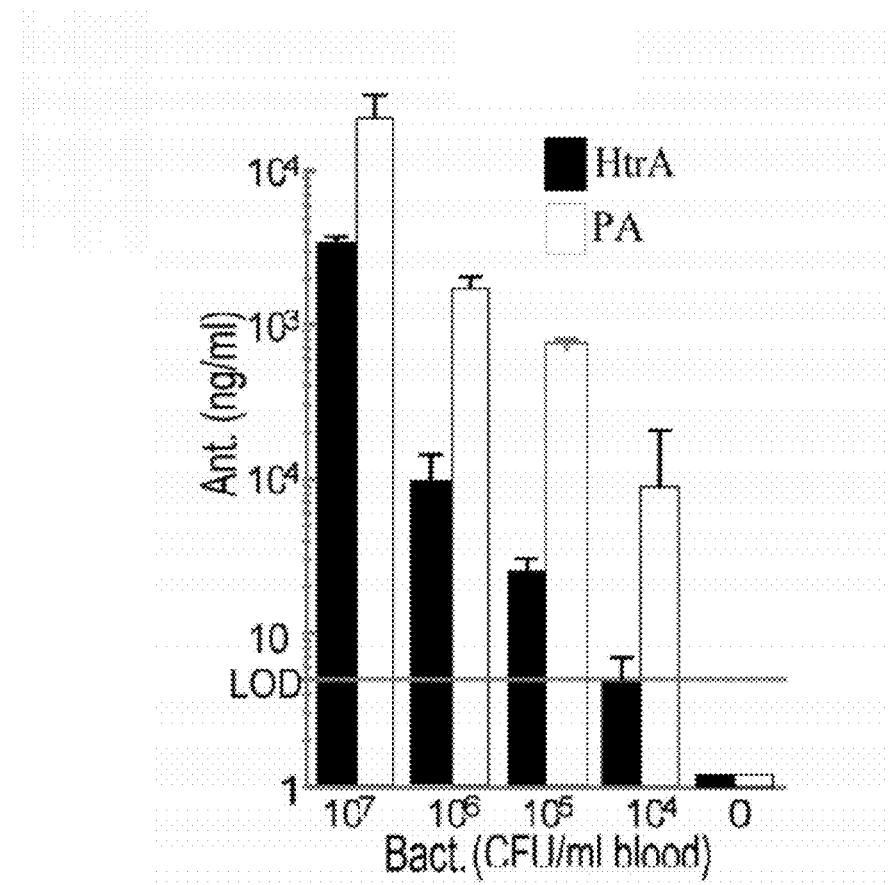
Figure 3B:
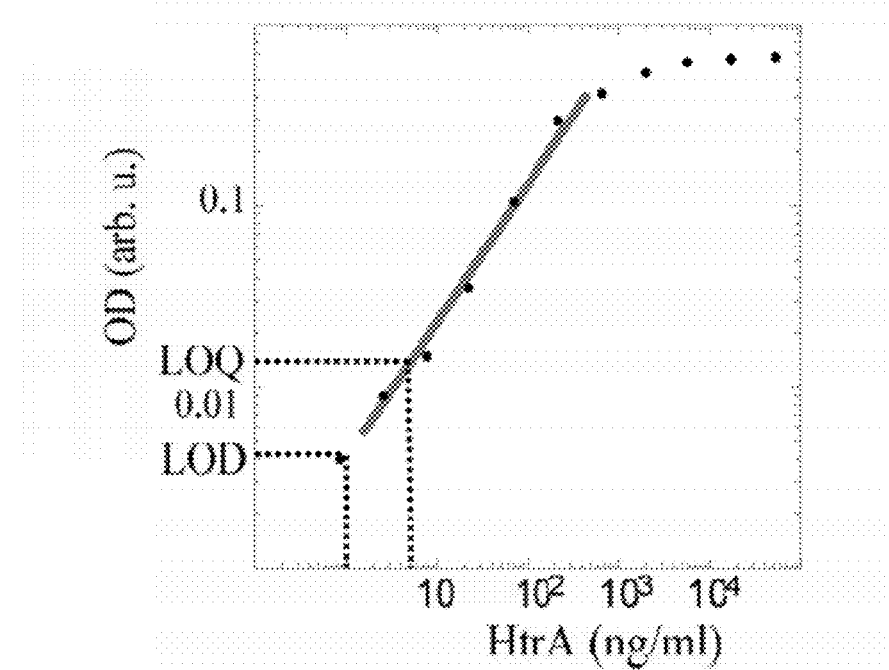
Figure 3C:
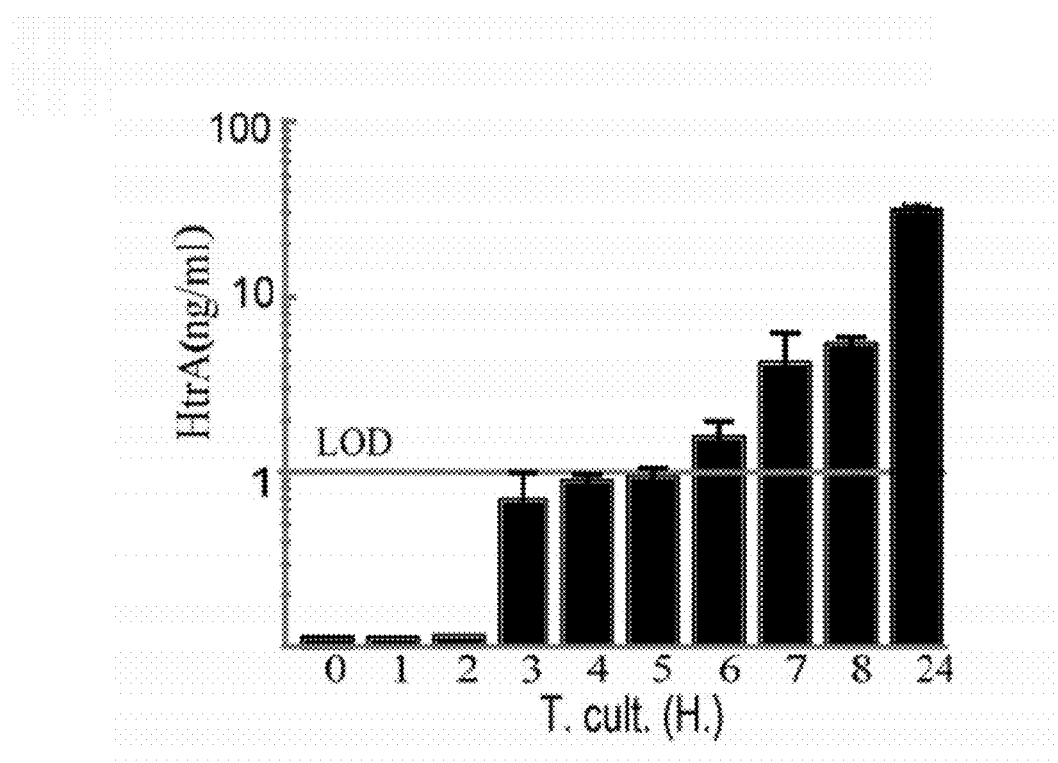

FIG. 3A-3C: Detection of HtrA and PA by capture ELISA.

Abbreviations: Ant.=Antigenemia; Bact.=Bacteremia; arb. u.=arbitrary units; T. cult.=Time in culture; H=hours.

FIG. 3A: Plasma samples collected from infected rabbits, exhibiting increasing levels of bacteremia were examined by a novel capture ELISA assay for detection and quantification of HtrA.

Histogram comparing the level of HtrA (black bars) and PA (gray bars) in same samples. PA concentration was determined using similar ELISA assays.

FIG. 3B: Calibration curve of the HtrA specific ELISA obtained with pure preparations of recombinant HtrA (R=0.996); the intercepts of the broken line with the abscissa and ordinate axes indicate the limit of detection (LOD-twice the background level) and the limit of quantification (LOQ, the lower value of the linear range of detection). The detection limit of the assay is 1 ng HtrA/ml of analyzed sample and the linear range for accurate quantification was determined as 5-2000 ng/ml. The assay requires 100 µl of serum. At least three duplicated assays were performed for each sample.

FIG. 3C: Histogram showing detection of HtrA over time in Bactec™ cultures inoculated with rabbit blood exhibiting $10^3$ CFU/ml.

FIG. 4A-4C: The proteins HtrA, BA0796 and BA1952 are specific for *B. anthracis*; the phylogenetically related *B. cereus* and *B. thuringiensis* secrete non-significant amounts of the biomarkers.

Abbreviations: Tot. prot. st.=Total protein stain; We. BL=Western Blot; T.=Time; H.=Hours; Turb.=Turbidity; Str.=Strain.

FIG. 4A: Filtered supernatants collected from *B. anthracis, B. cereus, B. thuringiensis* and *B. subtilis* rich medium-cultures, 24 hours post inoculation were examined by Western blot using specific antibodies against HtrA, BA0796 and BA1952.

FIG. 4B: Graph showing the growth curve of the various strains. Cultures of the different strains exhibited similar growth profiles.

FIG. 4C: Histogram showing quantification of HtrA in the culture of the different strains. Quantification was performed using the ELISA protocol as briefly described in FIG. 3B.

A, C, T, S represent the strains *B. anthracis, B. cereus, B. thuringiensis* and *B. subtilis*, respectively.

FIG. 5: Amino-acid sequence of the *Bacillus anthracis* biomarkers described herein: BA3660, BA1952 and BA0796.

DETAILED DESCRIPTION OF THE INVENTION

A search for novel diagnostic bacterial biomarkers indicative of infection with *B. anthracis* was carried out in peripheral blood of rabbits using a battery of specific antibodies. These antibodies were generated against antigens which the inventors had previously shown to be secreted by *B. anthracis*.

Until now, the only bacterial secreted proteins which could be directly detected in the circulation of infected animals were the toxin components PA, LF and EF (albeit the last two in very low amounts and only at late stages of infection, Kobiler et al., 2006; Dal Molin et al., 2008).

According to the invention, at least three additional secreted proteins were detected in the circulation of infected animals: the chaperone and protease HtrA (locus tag BA3660), an endopeptidase (BA1952) belonging to the NlpC/P60 family of proteases, and the product of the locus BA0796—a protein of unknown function. Visualization of the bacterial proteins by Western blot analysis in the circulation of infected animals was achieved following depletion of highly abundant serum proteins by an affinity protocol for relative enrichment of scarce serum proteins. These three proteins could be detected in plasma samples from infected animals exhibiting $10^3$ or more cfu/ml and also in standard blood cultures 3 to 6 hours post inoculation with blood at a bacteremic level as low as $10^3$-cfu/ml. The chaperone and protease HtrA could be detected directly in the circulation at an early stage of bacteremia, and all three proteins were detected in standard clinical cultures initiated from early infection blood samples at a bacteremic level of $10^3$ cfu/ml, compatible with post-exposure therapy. Using a novel ELISA test (which does not require pre-removal of abundant proteins) HtrA could be accurately quantified in bacteremic blood samples (approximately 5 µg protein/ml of blood exhibiting $10^6$ cfu/ml). The appearance of HtrA in the blood of infected rabbits at detectable levels almost coincides with that of the toxin component PA. This invention is the first documentation of direct detection of *B. anthracis* bacterially secreted proteins, other than the toxin components, in the circulation of infected animals. All three novel biomarkers, individually or collectively may serve for diagnosis of *B. anthracis* infection.

The following nomenclature is used herein when referring to the secreted proteins subject of the invention:

HtrA, the protein specified by the locus BA3660, is interchangeably referred to herein as HtrA, BA3660 or HtrA (BA3660); and its sequence represented by SEQ. ID. NO:1 (FIG. 5);

the NlpC/P60-domain endopeptidase specified by the locus BA1952, is interchangeably referred to herein as NlpC/P60-domain endopeptidase, BA1952 or NlpC/P60-domain endopeptidase (BA1952); and its sequence represented by SEQ. ID. NO:2 (FIG. 5);

the protein specified by the BA0796 locus is also referred to herein as BA0796; and its sequence represented by SEQ. ID. NO:3 (FIG. 5).

The herein used nomenclature of *Bacillus anthracis* genes, namely BA followed by a 4-digit number, refers to the tags of the respective genes in the NCBI data base, in the genome of the reference *B. anthracis* bacterial strain "Ames Ancestor", widely accepted in the *B. anthracis* field—note that in some publications, the gene tag is composed of the letters GBAA followed by a 4 digit number. The NCBI data base includes today sequences of several *B. anthracis* strains. In many cases, the same protein may appear in separate entries of the NCBI databank as a result of multiple submissions. In these cases, the proteins bear the same locus tag. In other *B. anthracis* strains, the orthologs of the proteins described in this invention have strain-characteristic tag numbers. It is conceivable that in the future, many more genomes will be available in the database, as additional *B. anthracis* strains (isolates) will be sequenced and annotated. In this case, the proteins described herein may be assigned yet additional tags. By convention, we shall consider that proteins from different *B. anthracis* isolates are orthologs, (representing the same proteins as those described in this invention), when they exhibit similarity over more than 80% of their sequence with respect to each protein (expectation value $E\delta e^{-10}$).

Thus, in a first aspect, the invention relates to a method for the diagnosis of *B. anthracis* infection in a test sample, said method comprising the steps of:

(a) providing at least one recognition-agent which specifically recognizes a *B. anthracis* specific bio-marker selected from the group consisting of HtrA (BA3660), NlpC/P60-domain endopeptidase (BA1952), and the protein specified by the BA0796 locus (BA0796), or of any fragment or derivative thereof;

(b) contacting an aliquot of said test sample with at least one recognition-agent of (a) under conditions allowing the interaction of said at least one recognition agent to said at least one *B. anthracis* specific bio-marker; and (c) detecting the interaction of said at least one recognition agent with said at least one *B. anthracis* specific bio-marker by suitable means and thereby the presence of said at least one bio-marker in said sample;

whereby detection of the presence of said at least one *B. anthracis* specific bio-marker indicates that said sample is infected with *B. anthracis*.

It may be understood that if such a sample (wherein the presence of at least one *B. anthracis* specific bio-marker has been detected) is obtained from an animal or human subject, said subject is infected with *B. anthracis*.

A "fragment" of a molecule, such as a fragment of the BA 3660, BA1952 or BA0796 proteins of the present invention is meant to refer to any amino acid subset of the molecule. A "variant" of such molecule is meant to refer to a naturally occurring molecule substantially similar to either the entire molecule or a fragment thereof. An "analog" of a molecule is a homologous molecule from the same species or from different species. By "functional" is meant having same biological function, for example, required for being recognized by the recognizing agent described herein. One example of a functional fragment is the amino acid sequence or region of the molecule that functions as an epitope for antibody recognition. Another example of a functional fragment is the region of the molecule that would present enzymatic activity. By "functional fragments" is meant "fragments", "variants", "analogs" or "derivatives" of the molecule having the same or substantially similar biological function as the full length protein.

The terms derivatives and functional derivatives as used herein mean peptides comprising the amino acid sequence of any one of BA3660, BA1952 and BA0796, with any insertions, deletions, substitutions and modifications (i.e., any mutation) to the protein that do not interfere with the ability of said protein to exhibit its biological function or to be recognized by a specific antibody. A derivative should maintain a minimal homology to said amino acid sequence, e.g. even less than 30%. It should be appreciated that the term "insertions" as used herein is meant any addition of amino acid residues to the peptides of the invention, between 1 to 50 amino acid residues, preferably, between 20 to 1 amino acid residues and most preferably, between 1 to 10 amino acid residues.

Thus, said *B. anthracis* bio-marker, in particular BA3660, BA1952, and BA0796, or of any fragment or derivative thereof, may be recognized or detected through binding to an antibody specific to said bio-marker.

Recognition by a recognition agent of a *B. anthracis* specific bio-marker may be followed by binding, or binding may be part of how recognition is achieved. Still, or in addition, binding may be how detection is achieved.

Alternatively, said *B. anthracis* specific bio-marker, in particular BA3660, BA1952 and BA0796, or of any fragment or derivative thereof, may be recognized or detected through their biological activity or structural feature. One example would be the detection through enzymatic activity, wherein an enzyme substrate would be the recognition agent. In such case, recognition and possibly binding would lead to an observable alteration or change in the enzyme substrate.

The recognition agent may therefore be a protein-based, carbohydrate-based, lipid-based, natural organic-based, synthetically derived organic-based, or inorganic-based material, or any small molecule.

Thus, in one particular embodiment of the present invention, said recognition-agent used in the methods, uses and kits described in the invention is an antibody specific for a *B. anthracis* specific bio-marker selected from the group consisting of BA3660, BA1952 and BA0796, or of any fragment or derivative thereof.

Accordingly, in the present study the inventors show that three proteins—the serine protease HtrA (BA3660), the NlpC/P60 family-endopeptidase (BA1952) and the product of the gene BA0796, a protein of unknown function, can be detected in blood samples drawn from infected rabbits (illustrated, inter alia, in FIG. 2A-2D). Interestingly, HtrA could be detected directly in blood samples at a low level of bacteremia ($10^3$ cfu/ml), compatible with post-exposure prophylactic treatment. All three biomarkers could be detected in blood cultures set with the blood of low bacteremic level; notably, BA0796 could be detected in this blood cultures as early as 2 hours post inoculation.

In this context, the present invention provides an antibody, or a fragment thereof, for use in the detection of *B. anthracis* infection in a sample, wherein said antibody recognizes and binds a *B. anthracis* bio-marker, and said bio-marker is one of BA3660, BA1952, and BA0796.

The three novel biomarkers may be used alone or in combination with each other (or with other biomarkers) as diagnostic tools. It is possible to predict that the sensitivity of detection assays using a combination of at least two biomarkers could be significantly improved, thus lowering the detection threshold of the biomarkers and enabling diagnosis of even lower levels of bacteremia.

Thus, both in the methods of the invention and in the kit provided herein, said sample to be tested for the presence of *B. anthracis* infection may be contacted with more than one recognition agent specific for each *B. anthracis* specific bio-marker, and detection of more than one of said biomarkers in a sample may be effected simultaneously. One example would be the use of at least two of the antibodies against said *B. anthracis* specific bio-markers in the reaction solution to be contacted with said sample.

The term "sample" in the present specification and claims is used herein in its broadest sense. It is meant to include both biological and environmental samples. Harvesting of these samples may be for (without being restricted to) diagnostic, forensic or epidemiologic purposes. A sample may include a specimen of natural or synthetic origin. Biological samples may be obtained from: an animal, particularly mammals including humans, a fluid, a solid (e.g., stool) or a tissue, as well as liquid and solid food and feed products and ingredients such as dairy items, vegetables, meat and meat by-products, and waste.

The term "sample" may also include body fluids (urine, blood, etc.), swabs taken from suspected body regions (throat, vagina, ear, eye, skin, sores), food products (both solids and fluids), swabs (taken from medicinal instruments, apparatus, materials), samples taken from air (for airborne bacteria especially from ventilation systems), samples taken from the environment (soil, water, plant parts). Typically swabs and samples that are a priori not liquid are contacted with a liquid medium which is then contacted with the detecting agent. Any said environment sample may serve as an inoculum for a bacterial culture which will represent the examined sample.

Biological samples may be obtained from all of the various families of domestic animals and livestock, as well as feral or wild animals, including, but not limited to, such animals as ungulates, bear, lagomorphs, rodents, etc. In one specific embodiment, biological samples are obtained from mammals, particularly humans.

In one particular embodiment of the invention, said sample to be used in the method of the invention is any one of a body fluid or a culture-derived sample.

A culture-derived sample may be a cell extract, a medium sample, or a culture from a body fluid, e.g. a culture of a blood sample.

It should be further noted that specific examples of body fluid samples are blood, serum, plasma, urine, saliva, phlegm, faeces, tissue extract, milk, cerebrospinal fluid, rinse fluid obtained from wash of body cavities and pus. Where mentioned in the method of the invention suitable means, said suitable means may be an immune affinity procedure, an enzymatic assay, or means for detecting a structural feature, amongst others.

Where said suitable means are an immune affinity procedure, said procedure is any one of enzyme-linked immunosorbent assay (ELISA), Western Blot, immuno-precipitation, FACS, Lateral Flow, Biochip arrays (Lim et al., 2005; Ewalt et al., 2001). An immunoassay may involve the detection of primary antibodies or secondary labeled antibodies conjugated to any fluorescence substance such as (but not limited to) those incorporating lanthanides, compatible with detection by Time-Resolved Fluorometry (TRF, which is based on the use of antibodies conjugated to a fluorescence substance exhibiting a large Stoke shift and a slow decay of the emitted fluorescence which may be consequently measured at high resolution) using any suitable fluorescence detection device (Peruski et al., 2002). Immunoassay may be any assay which is based on ECL (Electrochemical luminescence) involving the use of antibodies or antibody fragments conjugated to substances such as (but not limited to) ruthenium, where detection is mediated by any suitable device (such as the BioVeris platform, Rivera et al., 2006). Such detection modalities were described before and are known to persons skilled in the field of immunodetection (for example, Lim et al., 2005).

As an illustration of such suitable means, Example 3 and FIGS. 3A-3C presented herein demonstrate that HtrA could be detected in bacteremic blood in significant amounts (5 µg/ml), at a bacteremic level of $10^7$ cfu/ml blood, as well as in blood cultures, using an ELISA test, which may be used as a diagnostic tool. In addition, all three biomarkers could be detected by Western analysis in clinical cultures inoculated with blood exhibiting $10^3$ cfu/ml.

ELISA is a widely used method for the detection of specific proteins in a tissue sample. It involves the immobilization of an antibody (primary antibody) to a solid support such as plastic microplates, and detecting a specific antigen via binding to the immobilized antibody, followed by addition of secondary antibody or antibodies, the latter usually being conjugated to enzymes such as alkaline phosphatase or horseradish peroxidase in order to facilitate detection. Addition of a chemical substrate of the enzyme results in the development of a colored reaction product, which indicates the presence of the antigen of interest in the sample.

Hence, according to one embodiment, the immune affinity procedure may be an enzyme-linked immunosorbent assay (ELISA) selected from the group consisting of direct enzyme-linked immunosorbent assays, indirect enzyme-linked immunosorbent assays, direct sandwich enzyme-linked immunosorbent assays, indirect sandwich enzyme-linked immunosorbent assays, and competitive enzyme-linked immunosorbent assays.

In one particular embodiment, detection is effected through capture ELISA.

Capture ELISA (also known as "sandwich" ELISA) is a sensitive assay to quantify picogram to microgram quantities of substances (such as hormones, cell signaling chemicals, infectious disease antigens and cytokines). This type of ELISA is particularly sought after when the substance to be analyzed may be too dilute to bind to the polystyrene microtiter plate (such as a protein in a cell culture supernatant) or does not bind well to plastics (such as a small organic molecule). Optimal dilutions for the capture antibody, samples, controls, and detecting antibodies as well as incubation times are determined empirically and may require extensive titration. Ideally, one would use an enzyme-labeled detection antibody. However, if the detection antibody is unlabeled, the secondary antibody should not cross-react with either the coating antibody or the sample. Optimally, the appropriate negative and positive controls should also be included.

The capture or coating antibody to be used should be diluted in carbonate-bicarbonate buffer or PBS. Capture antibodies are typically plated at 0.2 to 10 µg/ml. It is preferable to use affinity purified antibodies or at a minimum use an IgG fraction. Generally samples are diluted in PBS in the 10 ng-10 µg/well range (the more sensitive the assay, the less sample is required).

Detection of the biomarkers of the invention, in particular detection of BA3660, BA1952 and BA0796, or of any fragment or derivative thereof, may be performed using antibodies which are specific to said biomarkers. These antibodies may be labeled directly or indirectly by a detectable moiety.

As used herein in the specification, the term "detectable moiety" refers to any atom, molecule or a portion thereof, the presence, absence or level of which may be monitored directly or indirectly. One example includes radioactive isotopes. Other examples include (i) enzymes which can catalyze color or light emitting (luminescence) reactions and (ii) fluorophores. The detection of the detectable moiety can be direct provided that the detectable moiety is itself detectable (i.e. can be directly visualized or measured), such as, for example, in the case of fluorophores. Alternatively, the detection of the detectable moiety can be indirect. In the latter case, a second moiety which reacts with the detectable moiety, itself being directly detectable is preferably employed. The detectable moiety may be inherent to the antibody. For example, the constant region of an antibody can serve as an indirect detectable moiety to which a secondary antibody having a direct detectable moiety can specifically bind.

Thus, secondary antibodies are particular suitable means for the detection of the anti-biomarker antibody in the method of the invention. This secondary antibody may be itself conjugated to a detectable moiety. One of the ways in which an antibody in accordance with the present invention can be detectably labeled is by linking the same to an enzyme. The enzyme, in turn, when exposed to an appropriate substrate, will react with the substrate in such a manner as to allow its detection, for example by producing a chemical moiety which can be detected, for example, by spectrophotometric, fluorometric or by visual means. Enzymes which can be used to label the antibody include, but are not limited to, horseradish peroxidase, alkaline phosphatase, malate dehydrogenase, staphylococcal nuclease, delta-5-steroid isomerase, yeast alcohol dehydrogenase, alpha-glycerophosphate dehydrogenase, triose phosphate isomerase, asparaginase, glucose oxidase, beta-galactosidase, ribonuclease, urease, catalase, glucose-6-phosphate dehydrogenase, glucoamylase and acetylcholinesterase, or any other enzyme which can be conjugated to an antibody and its reaction with a substrate, measured (or detected).

The detection can be accomplished by colorimetric methods, which employ a chromogenic substrate for the enzyme. Detection may also be accomplished by visual comparison of the extent of enzymatic reaction of a substrate in comparison with similarly prepared standards.

The solid support to which the first antibody is bound may be any water-insoluble, water-insuspensible, solid support. Examples of suitable solid support include large beads, e.g., of polystyrene, filter paper, test tubes, and microtiter plates. The first antibody may be bound to the solid support by covalent bonds or by adsorption. The advantage of the use of a solid support is that no centrifugation step is needed for the separation of solid and liquid phase.

The solid support mentioned above can include polymers, such as polystyrene, agarose, SEPHAROSE®, cellulose, glass beads and magnetizable particles of cellulose or other polymers. The solid-support can be in the form of large or small beads or particles, tubes, plates, or other forms.

As a solid support, use is preferably made of a test tube, or a microtiter plate the inner walls of which are coated with a first antibody, e.g., the antibodies specific to BA3660, BA1952 and BA0796, or of any fragment or derivative thereof prepared by the inventors for the present invention.

The sample to be used in the method of the invention may optionally undergo an affinity enrichment step before step (b) of the method, i.e., before the step of contacting an aliquot of said sample with said recognition agent. In particular, said affinity enrichment step may comprise passing said sample, for example blood, through a solid phase chromatography procedure.

Solid phase chromatography may be performed such that binding to the solid phase may be achieved by column chromatography, whereby the solid medium is packed onto a chromatography column, the sample run through the column to allow binding, a wash buffer run through the column and the elution buffer subsequently applied to the column and collected. Alternatively, binding may be achieved using a batch treatment, by adding the sample to the solid phase in a vessel, mixing, separating the solid phase (by centrifugation for example), removing the liquid phase, washing, re-centrifuging, adding the elution buffer, re-centrifuging and removing the eluate. Sometimes a hybrid method is employed, whereby the binding to the sample is done by the batch method, then the solid phase with the target molecule (i.e., the biomarkers) bound is packed onto a column and washing and elution are done on the column.

A third method, expanded bed adsorption, which combines the advantages of the two chromatographic methods mentioned above, is also possible. The solid phase particles are placed in a column where liquid phase is pumped in from the bottom and exits at the top. The gravity of the particles ensures that the solid phase does not exit the column with the liquid phase.

Reference to "determining" as used by the methods of the present invention, includes estimating, quantifying, calculating or otherwise deriving the amount of biomarker present in a specific sample. This may be achieved by measuring an end point indication that may be for example, the appearance of a detectable product, any detectable change in e.g. substrate levels or any change in the rate of the appearance of the product or the disappearance of the substrate, or measuring the amount of antibody bound to a biomarker as described by the invention.

As shown in the Examples, all three biomarkers could be detected by Western analysis in clinical cultures inoculated with blood exhibiting $10^3$ cfu/ml. after only 6-7 hours in culture. Remarkably, the protein BA0796 was detected as early as three hours following the onset of the culture, coinciding with the appearance in culture of PA, the only anthrax biomarker acknowledged before the present study (not shown). Therefore, the time of detection of specific B. anthracis biomarkers, namely BA3660, BA1952 and BA0796, in the method provided by the present invention, is much earlier than the routinely accepted 24 hours culture for diagnosis of infection in the clinical practice.

The term "rapid" appears to have varying meanings to microbiologists. The literature lists many articles claiming rapid analysis techniques, where rapid is defined as less than twenty four hours. The present invention relates to the novel methods in which analysis is possible in about two hours of culture, or possibly three, four, five, six or seven hours, including any fraction of the hour. Hence, the present invention provides a rapid diagnostic method for B. anthracis infection.

In another aspect the present invention provides a kit for the diagnosis of B. anthracis infection in a test sample, said kit comprising the following components:

(a) at least one recognition-agent which specifically recognizes at least one B. anthracis specific bio-marker selected from the group consisting of BA3660, BA1952 and BA0796, or of any fragment or derivative thereof; and (b) instructions for carrying out the detection of the presence of at least one B. anthracis bio-marker in a sample.

Said kit may optionally further comprise at least one of the following components:

(a) at least one means for collecting a sample to be tested;

(b) at least one compartment containing at least one recognition-agent which specifically recognizes at least one B. anthracis specific bio-marker selected from the group consisting of BA3660, BA1952 and BA0796, or of any fragment or derivative thereof;

(c) at least one reagent necessary for recognition of at least one of said recognition-agent to at least one of said B. anthracis specific bio-marker;

(d) at least one assay reagent for enabling detection of said recognition indicating the presence of said at least one biomarker; and (e) at least one control sample.

In all of herein described kits, said means for collecting a sample to be tested can be a swab, a pipette, or similar collection means and said incubation means can be a liquid or semisolid culture medium placed in a plate, test tube, a glass or plastic surface, a well, or on a strip of absorbent paper, or similar means.

It should be appreciated that any version of the kit has been designed so as to also allow the test to be run on a scanner and the results fed into the computer in real time. This will ensure that the entire information can be mailed directly to all concerned and that it will be stored intact for any future reference.

The recognition agent may be an antibody specific to said bio-marker, for example an antibody specific to any one of B. anthracis specific bio-markers described herein, in particular an antibody specific to BA3660, BA1952 and BA0796, or of any fragment or derivative thereof. Alternatively, said recognition agent is a substance that recognizes or detects said biomarkers, in particular BA3660, BA1952 and BA0796, or of any fragment or derivative thereof, through their biological activity or structural feature. One example of biological activity is an enzymatic activity, wherein an enzyme substrate would be the recognition agent. In such case, recognition and possibly binding would lead to an observable alteration or change in the catalytic activity of said enzyme or of the enzyme substrate.

The recognition agent may therefore be a protein-based, carbohydrate-based, lipid-based, natural organic-based, synthetically derived organic-based, or inorganic-based material, or any small molecule.

In one particular embodiment of the kit provided herein, said recognition-agent is an antibody specific for a *B. anthracis* specific bio-marker selected from the group consisting of BA3660, BA1952 and BA0796, or of any fragment or derivative thereof.

In another embodiment of the kit, said sample is any one of a body fluid and a culture-derived sample.

In a further embodiment of the kit provided herein, said recognition of said recognition-agent to said *B. anthracis* specific bio-marker is detected by suitable means. Suitable means may be an immune affinity procedure, an enzymatic assay, or means for detecting a structural feature, amongst others.

In another further embodiment, said recognition of recognition-agent to said *B. anthracis* specific bio-marker is achieved through an immune affinity procedure is any one of enzyme-linked immunosorbent assay (ELISA), Western Blot, immuno-precipitation, FACS, Biochip array, Lateral Flow, Time Resolved Fluorometry, ECL procedures, or any procedure based on immune recognition.

It should be noted that the kit of the invention may comprise in one compartment an array comprising at least one recognition agent, wherein each of said recognition-agents is located in a defined position in said array.

The term "array" as used by the methods and kits of the invention refers to an "addressed" spatial arrangement of the recognition-agent. Each "address" of the array is a predetermined specific spatial region containing a recognition agent. For example, an array may be a plurality of vessels (test tubes), plates, micro-wells in a micro-plate each containing a different antibody. An array may also be any solid support holding in distinct regions (dots, lines, columns) different and known recognition agents, for example antibodies. The array preferably includes built-in appropriate controls, for example, regions without the sample, regions without the antibody, regions without either, namely with solvent and reagents alone and regions containing synthetic or isolated proteins or peptides, corresponding to the biomarkers (positive control). Solid support used for the array of the invention will be described in more detail herein after, in connection with the kits provided by the invention.

A solid support suitable for use in the kits of the present invention is typically substantially insoluble in liquid phases. Solid supports of the current invention are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, filters, conducting and non-conducting metals, glass (including microscope slides) and magnetic supports. More specific examples of useful solid supports include silica gels, polymeric membranes, particles, derivatized plastic films, glass beads, cotton, plastic beads, alumina gels, and polysaccharides such as SEPHAROSE®, nylon, latex bead, magnetic bead, paramagnetic bead, superparamagnetic bead, starch and the like.

It should be further noted that any of the reagents included in any of the methods and kits of the invention may be provided as reagents embedded, linked, connected, attached placed or fused to any of the solid support materials described above.

Further, the present invention provides the use of an antibody or a fragment thereof, which specifically recognizes and binds a *Bacillus anthracis* bio-marker, in the preparation of a composition for detecting *Bacillus anthracis* infection in a sample, wherein said bio-marker is one of BA3660, BA1952 and BA0796.

Interestingly, in addition to the specific antibodies to BA3660, BA1952 and BA0796, which have been described herein, other antibodies specific for 21 other secreted proteins prepared as well by the present inventors through the DNA vaccination method as described in the Examples, did not show recognition of any specific marker in the peripheral blood of infected animals. These antibodies were directed against the following *B. anthracis* proteins (enumerated below according to their respective locus tag number in the NCBI database), all selected on the basis of the previous genomic, proteomic and serologic surveys conducted by the inventors (Chitlaru et al., 2004, 2006, 2007; Gat et al., 2005, 2006, 2008): BA0345, BA0656, BA672, BA0799, BA0855, BA0898, BA1295, BA2805, BA2849, BA3189, BA3367, BA3668, BA4766, BA4786, BA4787, BA4788, BA4789, BA5330, BA5427, pXO1-54 (tagged in the NCBI data bank as GBAA_pXO1-54__0079) and pXO1-130 (tagged in the NCBI data bank as GBAA_pXO1-130__0197). The fact that only three amongst the overall 24 antibodies tested enabled detection of their cognate antigens underlines the fact that the recognition of the three biomarkers documented in this invention is a surprising outcome of the previous studies of the inventors.

The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments, which retain the ability to bind their specific epitope. Such fragments can be obtained commercially or using methods known in the art. For example F(ab)$_2$ fragments can be generated by treating the antibody with an enzyme such as pepsin, a non-specific endopeptidase that normally produces one F(ab)$_2$ fragment and numerous small peptides of the Fc portion.

As used herein, the term antibody is intended to include intact molecules, such as a naturally occurring, synthetic or recombinant antibody, a chimeric antibody, as well as fragments thereof, such as for example, scFv, Fv, Fab', Fab, diabody, linear antibody or F(ab')$_2$ antigen binding fragment of an antibody which are capable of binding the antigen.

The generation of polyclonal antibodies against proteins is described, inter alia, in Chapter 2 of Current Protocols in Immunology, John E. Coligan et al. (eds.), Wiley and Sons Inc.

Monoclonal antibodies may be prepared from B cells taken from the spleen or lymph nodes of immunized animals, in particular rats or mice, by fusion with immortalized B cells under conditions which favor the growth of hybrid cells. The technique of generating monoclonal antibodies is described in many articles and textbooks, such as the above-noted Chapter 2 of Current Protocols in Immunology. Spleen or lymph node cells of these animals may be used in the same way as spleen or lymph node cells of protein-immunized animals, for the generation of monoclonal antibodies as described in Chapter 2 therein. The techniques used in generating monoclonal antibodies are further described in by Kohler and Milstein [Kohler and Milstein (1975) Nature 256; 495-497] and in U.S. Pat. No. 4,376,110.

Fab and F(ab')2 and other fragments of antibodies are typically produced by proteolytic cleavage, using enzymes such as papain (to produce Fab fragments) or pepsin (to produce F(ab')2 fragments).

Further to anthrax early and rapid diagnostic, the biomarkers described herein, in particular BA3660, BA1952 and BA0796, may serve for further monitoring of subjects that may or may not be previously identified as infected with *B. anthracis*, in order to confirm previous exposure. The identification or diagnosis of previous *B. anthracis* infection may be through detection of said biomarkers in samples obtained from said subjects or, alternatively, through the detection of circulating antibodies against said biomarkers (clearly at a stage further to seroconversion) in such infected subjects. Another alternative scenario is that of subjects who may have been treated for bacterial infection, even without specific diagnosis of anthrax, and thus a specific diagnostic of anthrax may be desirable, for example for epidemiological purposes. In another scenario, one may envisage a situation in which a subject, in particular one among bio-terror or calamity first responder personnel, has been vaccinated against anthrax with a vaccine based on one antigen, and so the use of an alternative detection modality, based on a different antigen, may be imperative.

Therefore, the product of any one of BA3660, BA1952 or BA0796, as herein described, may be used for the monitoring or detection of anthrax infection.

Thus, in an even further aspect the present invention provides the use of a *Bacillus anthracis* protein or a fragment thereof in the preparation of a composition for detecting *Bacillus anthracis* infection in a sample, wherein said protein is one of BA3660, BA1952 and BA0796.

The preparation of pharmaceutical compositions is well known in the art and has been described in many articles and textbooks, see e.g., Remington's Pharmaceutical Sciences, Gennaro A. R. ed., Mack Publishing Company, Easton, Pa., 1990, and especially pages 1521-1712 therein.

It is important to mention that all three biomarkers described herein exhibit specificity with respect to *B. anthracis*. As it will be apparent from the examples, in contrast to *B. anthracis*, the closely related bacillus strains *B. cereus* and *B. thuringiensis* do not secrete significant amounts of the three biomarkers into the culture media, nor does the more distant *B. subtilis* strain. In addition, all three biomarkers exhibit universality with respect to their ability to serve for detection of different *B. anthracis* strains: the respective genes are present in the genomes of all *B. anthracis* strains sequenced to this day (16 different strains available in the NCBI data base). Furthermore, proteomic data established expression of these markers in four different strains: ATCC14185, Vollum (Chitlaru et al., 2006), Sterne (Francis et al., 2005) and UM23C1-2 (Antelmann et al., 2005). Thus, it appears that the biomarkers meet both the specificity and the universality standards which facilitate their use in the development of diagnostic tools.

Thus, the *Bacillus anthracis* proteins described herein (or a fragment or derivative thereof) may be used as biomarkers for the diagnosis of anthrax in a subject, wherein said protein is one of BA3660, BA1952 and BA0796.

The present invention is defined by the claims, the contents of which are to be read as included within the disclosure of the specification.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the intended scope of the invention.

Unless defined otherwise, all technical and scientific terms used herein have the same meaning as commonly understood by one of ordinary skill in the art to which this invention is related.

EXAMPLES

Methods

A number of immunological techniques are not in each instance described herein in detail, like for example ELISA, as they are well known to the person of skill in the art, and these are described in detail in e.g., Harlow and Lane (1988) *Antibodies: a laboratory manual*, Cold Spring Harbour Laboratory.

Bacterial Strains

The *B. anthracis* strains used herein were: the fully virulent Vollum strain (pXO1$^+$; pXO2$^+$), and the attenuated strains ΔVollum (pXO1$^-$;pXO2$^-$) and Δ14185-HtrA (pXO1$^-$; pXO2$^-$). The latter represents an engineered strain overexpressing and secreting high amounts of the serine protease HtrA (TIGR tag BA3660). Expression is driven by the Sap promoter, following transfection of the Δ14185 strain with the appropriate expression vector. The Δ14185 platform strain is a pXO1-deleted derivative of the non-proteolytic vaccine strain V770-NP1-R referred by its ATCC accession number, ATCC14185. The platform strain, as well as the repertoire of plasmid vectors appropriate for heterologous overexpression of *B. anthracis* antigens was previously detailed (Gat et al., 2003, 2008; Cohen et al 2000; Mendelson et al., 2003). Other bacterial cultures used are *B. cereus* 14579, *B. thuringiensis*-subspecies *israeliensis* ATCC35646 and *B. subtilis* strain 168. All cultures were carried out in FAG media (Cohen et al., 2000) at 37° C. with vigorous shaking (250 rpm). Blood cultures were carried out in commercial clinical Bactec™ flasks, according to the specification of the manufacturer.

One Dimension (1D) SDS-PAGE and 2-Dimensional Electrophoresis (2DE)

For 1D-SDS-PAGE, samples were mixed with Laemmli sample buffer (2% SDS, 700 mM β-mercaptoethanol, Bio-Rad) and boiled for 5 minutes before loading.

For 2DE analysis, UREA buffer, containing 8M urea, 4% (w/v) CHAPS, 40 mM Tris, 2% Dithiothreitol (DTT) and 0.2

(w/v) BIO-LYTE® 3/10 (BioRad), was added to the protein mixtures (1:1) and loaded on 11 cm. IPG (Immobilized pH-gradient) strips (non-linear [NL] pH 3-10, Bio-Rad) for overnight. $1^{st}$ dimension isoelectric focusing (IEF) was carried out at 10,000 volt to a total 50,000V-hr, initiated by a slow step at 250 volt for 30 min. Strips were then processed for the second dimension separation by a 10 minutes incubation in 6M urea, 2% SDS, 0.375 M Tris-HCl (pH 8.8), 20% glycerol, 2% (w/v) DTT, followed by 10 minutes incubation in a similar solution in which the DTT was replaced by 2% iodoacetamide. Strips were applied to 12.5% SDS-PAGE gels and electrophoresis was carried out on a BioRad gel running System. Gels were stained with SeeBand Forte staining COOMASSIE® solution (GeVa, Beit Haemek, Israel) or transferred to nitrocellulose membrane for Western blot analysis.

Hyperimmune Anti-B. anthracis Antisera and Antibodies Specific for the Products of Individual Genes Guinea pig hyperimmune anti B. anthracis antiserum used in this study as a probe for visualization of B. anthracis exposed antigens on Western Blots was previously described (Chitlaru et al., 2007; Gat et al., 2006). This serum was collected from animals infected with $10^7$ spores of the highly attenuated mntA$^-$ mutant derived from the Vollum strain (Gat et al., 2005).

The antibodies against BA0345, BA0656, BA672, BA0796, BA0799, BA0855, BA0898, BA1295, NLP/P60 (BA1952), BA2805, BA2849, BA3189, BA3367, HtrA (BA3660), BA3668, BA4766, BA4786, BA4787, BA4788, BA4789, BA5330, BA5427, pXO1-130 (tagged in the NCBI data bank as GBAA_pXO1-130_0197), and pXO1-54 (tagged in the NCBI data bank as GBAA_pXO1-54_0079) proteins were generated by DNA vaccination as previously described (Grosfeld et al., 2005, Gat et al., 2006 and Chitlaru et al., 2007). In brief, individual open reading frames (ORFs) were cloned in the eukaryotic expression vector pCI (Promega), which carries the eukaryotic cytomegalovirus promoter, a recombinant chimeric intron and the simian virus 40 polyadenylation signal for efficient expression in mammalian cells, in addition to the T7 promoter for in vitro transcription and translation (T&T) expression (Gat et al., 2006, 2007; Grosfeld et al., 2003). Plasmid DNA for gene gun immunization was prepared by an alkaline lysis method followed by CsCl gradient centrifugation. The purified DNA preparations were solubilized in pyrogen-free water and kept frozen. Immunization protocols were essentially as described before (Grosfeld et al., 2003, Gat et al 2007). For the gene gun vaccination (Helios Gene Gun system, Bio-Rad), plasmid DNA was precipitated onto 1 µm diameter gold particles at a ratio of 2 µg per mg of gold and loaded onto Gold-Coat tubing (Bio-Rad) using polyvinylpyrrolidone as an adhesive. Gene-gun shots (0.5 µg DNA) were directed onto exposed abdominal dermis, and the protocol included 3-4 immunizations of mice (22-26 g females, ICR, Charles River Laboratories, Margate, United Kingdom) or Guinea pigs (250-300 g. females, Charles River Laboratories, Margate, United Kingdom) at 2-week intervals. Each DNA vaccination group included 10 experimental animals. Animals were bled for serum collection from the tail following each boost and by cardial puncture for the final bleeding. Determination of the immune response elicited in the animals following DNA immunization was determined by quantitative immunoprecipitation (IP) titration (data not shown) for the respective ORFs investigated using in vitro T&T products as previously described (Gat et al 2007).

Generation of Rabbit Sera Exhibiting Various Levels of Bacteremia

New Zealand White (NZW) rabbits (2.5-3.5 kg., Harlan, Israel) were infected with B. anthracis Vollum strain by subcutaneous administration of 15 50% Lethal Dose ($LD_{50}$), $150LD_{50}$, or $1500LD_{50}$ ($1LD_{50}=10$ spores). Serum was collected 24 and 36 hours following injection into sodium citrate tubes for bacteremia and into BD Vacutainer® tubes for haematocrit-free serum. The bacteremic level of each individual blood sample was determined by plating serial dilutions and colony counting. Serum collected from rabbits infected by the intranasal route of administration with B. anthracis spores of the Vollum strain, exhibiting a bacteremic level of $10^7$ CFU (colony forming units)/ml were kindly provided by Dr. Zeev Altboum, Israel Institute for Biological Research (see Kobiler et al., 2006).

Blood Cultures 10 ml of rabbit blood were collected into sodium citrate tubes, transferred to blood culture bottle (Bactec™, BD, final volume 25 ml) and incubated at 37° C. B. anthracis cells (final bacteremia level: $10^3$ CFU/ml) were inoculated into each bottle. Culture samples (1 ml) were taken every 1 hour for CFU counts (100 µl sample in decimal dilutions plated on LB plates overnight at 37° C.), and for Western blot analysis (900 µl). Cultures samples were centrifuge at 1800 g, 4° c. for 2 minutes in Microtainer®(BD) tubes for removal of haematocrit. The serum samples were directly subjected to Western blot analysis.

Enrichment of Scarce Proteins in Serum Using the Proteominer™ Affinity Chromatography Column The Proteominer™ (Bio-Rad) procedure is based on affinity chromatography of a complex mixture of proteins to a combinatorial library of hexapeptides immobilized on beads. This procedure reduces the dynamic range of protein concentrations in the sample by means of enhanced relative capacity for scarce proteins and rapid saturation of abundant protein ligands. 1 ml of serum was loaded on each Proteominer™ column which was processed according to the manufacturer indications. Elution of bound proteins was performed using a solution containing 300 µl 4M Urea, 1% CHAPS and 5% acetic acid. Samples were neutralized with 4M sodium carbonate to a pH 7-8 and purified using the 2D-clean up kit (Bio-Rad) prior to further analysis.

Quantification of PA by Enzyme-Linked Immunosorbent Assay (ELISA)

PA levels were determined by capture ELISA performed in 96-well microtiter plates (Nunc, Roskilde, Denmark) with purified PA (Reuveny et al., 2001) as a reference standard, as previously described (Kobiler et al., 2006). ELISA was carried out using the following antibodies: 100 µg/ml anti-PA rabbit serum for capturing (plate coating) and 100 µg/ml mouse anti-PA serum for detection. The assay was developed with goat alkaline-phosphatase conjugated anti-mouse IgG (Sigma), and visualized using the appropriate alkaline-phosphatase reagent.

Partial Purification of Recombinant HtrA, Generation of Rabbit Anti-HtrA Antibodies and Quantification of HtrA by Capture ELISA Recombinant HtrA synthesized and secreted by the B. anthracis Δ14185-HtrA strain was harvested from the filtered (0.22 µm Filter System, Corning, N.Y., USA) supernatant of 20 hrs FAG media cultures (which typically contain 40-60% recombinant HtrA) by 15% trichloro acetic acid (TCA) precipitation carried out by incubation at 4° C. for at least 8 hrs, followed by Sorvall centrifugation (>10000 rpm, 25 minutes, 1° C., SLA-1500 rotor). The proteinous pellet was resuspended in a 20 times smaller volume (compared to the initial culture volume) of phosphate buffer saline (PBS) by vigorous scrapping and re-centrifuged for removal of un-dissolved material. The resulting clear supernatant, typically consisting of more than 90% recombinant HtrA at a final concentration of 0.6-0.8 mg/ml, was divided into aliquots and stored at −70° C. until use. NZW female rabbits (3 Kg) were immunized by 4 consecutive 3 weeks-apart subcutaneous injections of 0.5 mg HtrA, emulsified with complete Freund's adjuvant (Sigma) for the first injection and incomplete Freund's adjuvant for the subsequent boosting. Presence of specific anti-HtrA antibodies was monitored by Western blot 12 days after each boost. Rabbits were sacrificed and bled terminally by cardiac puncture for the collection of immune sera. An ELISA test was established using the rabbit anti-HtrA antibodies for coating 96-wells micro-titer plates, as the capture reagent and the mouse anti-HtrA antibodies obtained by DNA immunization as the detection reagent. Visualization of signal was enabled by the use of anti-mouse Ig antibodies conjugated to alkaline phosphatase developed with the appropriate substrate. This quantitative assay requires 100 µl sample, and it is appropriate for direct inspection of serum samples (does not require pre-removal of abundant proteins). Quantification was based on calibration curves set with accurate amounts of purified preparations of HtrA; the detection limit of the assay is 1 ng HtrA/ml of analyzed sample and the linear range for accurate quantification was determined as 5-2000 ng/ml.

Animal Experimentation

All studies involving experimental animals were carried out according to the National Research Council 1996 Guide for the Care and Use of Laboratory Animals and approved by the Israel Institute of Biological Research (IIBR) Animal Use Committee.

Example 1

Detection of *Bacillus anthracis* Secreted Proteins in Blood Samples Collected from Infected Animals, Requires Removal of Abundant Serum Proteins Two approaches were considered for identification of bacterial proteins in plasma obtained from infected animals: global comparison of proteins from infected and naïve sera and examination of specific proteins in these sera using antibodies against specific pre-selected immunogenic bacterial proteins. Preliminary experiments, by both approaches, established that the overwhelming presence of highly abundant proteins (such as albumin and immunoglobulins [Ig]) limit the ability to detect additional proteins other than PA, even when quantities as high as 200 µg protein were loaded on gels (FIG. 1B). This complication of detection, which was previously described in numerous surveys of plasma proteins in search for disease biomarkers, is usually circumvented by depletion of abundant serum proteins (see for example Bjorhall et al., 2005; Ethan et al., 2005; Govoruchina et al., 2003; Wang et al., 2003; Ahmed et al, 2003; Righetti et al., 2006; Issaq et al., 2007). Different procedures including immunodepletion and/or diminution based on affinity of Ig and albumin to various compounds did not result in significant enrichment of scarce bacterial proteins. The inventors therefore employed a newly developed procedure which enables enrichment of scarce proteins in complex mixtures by means of affinity to a random combinatorial-ligand solid phase immobilized library (the Proteominer™ column; Righetti et al., 2006; Boschetti et al., 2007; Boschetti and Righetti, 2008). Contrary to procedures which exploit binding of the abundant proteins to an affinity column (for their removal), the Proteominer™ matrix preferentially binds the scarce proteins while the most abundant serum proteins are washed out in the chromatographic flow-through fraction (FIG. 1A). Indeed this affinity enrichment-step enabled visualization by standard protein staining of low quantity serum proteins whose detection was precluded by the presence of highly abundant proteins (see one-dimensional or two-dimensional PAGE gels, FIG. 1A).

The presence of bacterial antigens was initially investigated in highly bacteremic ($10^7$ cfu/ml) blood samples obtained from infected rabbits. The protein mixture released from the column was probed on Western blots with guinea pig total anti-*B. anthracis* antibodies (referred herein as "hyperimmune" serum). This hyperimmune serum was shown in previous serological studies to be efficient in identifying secreted and surface-associated *B. anthracis* antigens both by Western and immunoprecipitation protocols (Gat et al., 2006; Chitlaru et al., 2007). The data depicted in FIG. 1B clearly demonstrate that many bacterial proteins are present in the circulation of the infected animals, as compared to uninfected controls.

The enriched serum samples were resolved by high resolution 2D electrophoresis and attempts were made to identify by MALDI-TOF-MS tryptic-fingerprinting protein spots which may have represented bacterial proteins. Yet these attempts were not successful, given the fact that 2DE examination of plasma samples derived from infected animals and those taken from uninfected ones did not reveal the presence of bacterial protein at levels compatible with mass-spectroscopic identification (note similarity of COOMASSIE®-blue stained 2DE gels in FIG. 1B).

Example 2

Detection of *B. anthracis* Secreted Proteins in Bacteremic Sera Employing Specific Antibodies The alternative approach attempted for identification of bacterial proteins in sera of infected animals relied on the use of a battery of specific antibodies generated on the basis of the inventors' previous survey of *B. anthracis* immunogenic protein.

The inventors recently compiled a list of *B. anthracis* immunogenic secreted proteins based on extensive bioinformatics, proteomic and genomic screens corroborated by serological analysis and inspection of patterns of expression under conditions which recapitulate the infection process in the host (Ariel et al., 2003; Chitlaru et al., 2006 and 2007; Gat et al., 2006; see also Gat et al, 2008 for the Fe regulated membranal determinants of *B. anthracis*). This list provided a pool of potential vaccine and/or diagnostic markers, from which 24 proteins were selected for generation of antibodies (Table I), which would serve as a tool for examining their presence in blood samples directly obtained from infected animals or in blood cultures. To circumvent the need for laborious protein purification, the antibodies were generated by DNA vaccination of mice and guinea pigs using the respective ORFs cloned in an appropriate eukaryotic expression vector (Grosfeld et al., 2003).

All the proteins selected display functional domains compatible with a role in bacterial pathogenesis and/or represent putative homologs of virulence factors described in other pathogenic bacteria.

To probe the presence of these proteins in blood samples of sick animals, serum derived from infected rabbits (marked "I" in FIG. 2A), exhibiting $10^7$ cfu/ml, was subjected to affinity removal of abundant plasma proteins and inspected by Western blot analysis, in comparison to similarly processed serum derived from non-infected animals (marked "N" in FIG. 2A). As a positive control, the analysis included Western immunodetection of the toxin component PA; until the present study, the toxin proteins represented the only *B. anthracis*-derived secreted proteins that could be detected in the circulation of infected animals. The analysis revealed that three amongst the proteins selected could be detected in significant amounts in the bacteremic sera (FIG. 2A). These were the protease/chaperon HtrA (BA3660), the NlpC/P60-domain endopeptidase (BA1952) and the protein of unknown function specified by the locus BA0796. The proteins were detected in bacteremic sera irrespective of the route of infection (FIG. 2D). Most notably, these three chromosomally-encoded proteins belong to the group of highly immunogenic secreted proteins that were previously described (Chitlaru et al., 2007), and are expressed preferentially under culture conditions which are reminiscent of those encountered in the host. Furthermore their abundance in culture seems to depend on the presence of the native virulence plasmids PXO1 and PXO2 (Chitlaru et al., 2006). The full amino acid sequence of the three novel *B. anthracis* biomarkers described herein is provided in FIG. 5.

TABLE 1

Proteins tested as potential biomarkers in this invention.

| Accession number[a] | Protein | Symbol | Distinctive domains[b] | Putative function |
|---|---|---|---|---|
| BA0345 | Alkylhydroxyperoxide reductase | AhpC | | Oxidative stress response |
| BA0656 | SBP[c] of ABC transporter | — | S | Transport of Oligopeptides |
| BA0672 | Immune Inhibitor | InhA2 | S, Lipobox | Metalloprotease |
| BA0796 | Hypothetical | — | S, SH3x2, 3D | Unknown |
| BA0799[d] | Hypothetical | — | S, HlyD | Unknown |
| BA0855 | SBP of ABC transporter | — | S | Transport of amino-acids |
| BA0898 | Alanine amidase | CwlB | S, SLH | Cell-wall hydrolysis |
| BA1295 | Immune Inhibitor | InhA1 | S | Zn protease |
| BA1952 | NlpC/P60 family endopeptidase | — | S, SH3x2, NlpC/P60 | Cell-wall hydrolysis |
| BA2805 | Glycosyl hydrolase | — | | Cell-envelope associated hydrolase |
| BA2849 | Hydrolase | — | S, NlpC/P60 | Protease |
| BA3189 | SBP of ABC transporter | MntA | S, Lipobox | Transport of Mn |
| BA3367 | γ phage receptor | GamR | S, Sort | Unknown |
| BA3660 | Serine protease | HtrA | S | Chaperone, secretion, stress response |
| BA3668 | Glycosyl hydrolase | — | LysM | Cell-envelope associated hydrolase |
| BA4766 | SBP of ABC transporter | FhuD | S, Lipobox | Acquisition and transport of Fe |
| BA4786 | SBP of ABC transporter | IsdE | S, Lipobox | Acquisition and transport of Fe |
| BA4787 | Iron-regulated determinant | IsdK | S, NEATx5 | Acquisition and transport of Fe |
| BA4788 | Iron-regulated determinant | IsdJ | S, NEATx1 Sort | Acquisition and transport of Fe |
| BA4789 | Iron-regulated determinant | IsdC | S, NEATx1 Sort | Acquisition and transport of Fe |
| BA5330 | SBP of ABC transporter | FatB | S, Lipobox | Acquisition and transport of Fe |
| BA5427[e] | Endopeptidase | LytE | S, NlpC/P60 | Cell-wall hydrolysis |
| pXO1-54 | Unknown | — | S, SLH | Unknown |
| pXO1-130 | SBP of ABC transporter | AdcA | S, Lipobox | Transport of Zn |

The proteins which were detected in the circulation of the infected animals are shadowed.
[a]Proteins are arranged in ascending order according to their accession number which refers to the respective genomic locus tag (www.ncbi.nlm.nih.gov).
[b]Domains which are inherently related to the functional annotation of the proteins are not included. S, export signal peptide; SH3, Src homology domain; HlyD, homology domain to some proteins involved in toxin secretion in gram-negative bacteria; 3D cation binding domain involved in protein-protein interactions; SLH, S-layer homology domain; NEAT, "Near transporter" repeat domain present in ORFs adjacent to iron transporters in Gram-positive bacteria; Lipobox, characteristic domain for membranal anchorage of solute-binding subunits of bacterial ABC transporters; NlpC/P60, cell wall peptidase family domain; Sort, gram-positive sortase-mediated membrane retention domain.
[c]SBP, solute binding protein: the ligand recognition subunit of an ABC transporter.
[d]The product of the gene BA0799 is annotated as hypothetical of unknown function in the genomic data base, yet it may represent a component of an ABC transporter, based on its genomic location and sequence homology (Chitlaru et al., 2007).
[e]The product of the locus BA5427 is functionally annotated in the data base as the *B. anthracis* homologue of the known LytE *Bacillus* cell wall hydrolase, as indicated in the table. We note that the protein indeed exhibits an LytE like NlpC/P60 protease domain, yet it lacks the characteristic LysM domains (necessary for peptidoglycan targeting), therefore its functional annotation could be incorrect.

Example 3

Detection of *B. anthracis* Secreted Biomarkers at Low Levels of Bacteremia

Bacterial infections are usually diagnosed by tests of cultures inoculated with various clinical specimens (blood or other body fluids) obtained from sick individuals, and rarely by direct examination of the clinical samples.

Following the initial detection of *B. anthracis* biomarkers in the highly bacteremic sera, the inventors addressed the question whether these secreted proteins can be detected in sera obtained from animals at earlier stages of the infection, exhibiting lower levels of bacteremia, either by directly inspecting blood samples or in blood cultures. To answer this question, the inventors inspected by Western blot a battery of plasma samples obtained from infected rabbits exhibiting increasing levels of bacteremia for the presence of the three novel secreted biomarkers (FIG. 2A). The inventors observed that HtrA could be detected in blood samples displaying as low as $10^3$ cfu/ml while endopeptidase BA1952 and protein BA0796 could be detected in the circulation of rabbits exhibiting $10^5$ cfu/ml blood. To determine whether the biomarkers investigated in this study may serve for determination of *B. anthracis* presence in early blood cultures, sterile standard blood-culture bottles, such as those widely used for clinical diagnosis of bacterial infection, were inoculated with blood exhibiting $10^3$ cfu/ml. As expected, all three biomarkers identified in the blood samples were detected in the culture (FIG. 2B). Protein HtrA could be detected 6 hours post inoculation, the endopeptidase BA1952 about 7 hours following the onset of the culture, and most remarkably, the protein BA0796 was detected as early as 3 hours after the initiation of the blood culture (FIG. 2B). Other bacterial secreted proteins addressed in this study (Table I) could not be detected (not shown). It should be noted that in blood cultures all three biomarkers can be distinguished within a time window commensurate with the accepted culture time in clinical diagnosis routines, and the detection by Western-blot analysis of the biomarkers in blood cultures did not require removal of the abundant proteins, as in the case of direct inspection of blood samples.

Thus, the novel biomarkers can be detected either directly or following culturing of blood samples exhibiting $10^3$ bacteria/ml.

Example 4

Detection and Quantification of HtrA in Blood Samples by ELISA

In a preliminary feasibility study aimed at probing the possible use of HtrA, one of the novel biomarkers, as a diagnostic marker for *B. anthracis* infection, a capture ELISA test using rabbit anti-HtrA antibodies as the capture reagent and mouse anti-HtrA antibodies obtained by DNA-immunization as the detection reagent (FIG. 3A-3C) was developed. Using the rapid ELISA test, HtrA could be directly detected in significant amounts in infected rabbit sera at a bacteremic level as low as $10^4$ CFU/ml; notably, HtrA levels are commensurate to those of PA, the *B. anthracis* toxin component necessary for the onset of the disease (FIG. 3A). The assay does not require depletion of abundant serum proteins, and the high sensitivity of the assay detecting HtrA is in line with its classification as highly immunogenic in the inventors' previous seroconversion study of *B. anthracis* antigens (Chitlaru et al., 2007). Similarly to HtrA, proteins BA0796 and BA1952 could be detected by capture ELISA both in *B. anthracis* bacteremic sera and infected blood cultures (data not shown).

Example 5

Infection-Unique Biomarkers

Infections caused by bacilli of the *Cereus* group, phylogenetically related to *B. anthracis*, usually affect immunocompromised individuals or occur as opportunistic complications of prolonged hospitalization, traumatic or post-surgical wounds or use of invasive clinical devises (Drobniewski, 1993). Despite the fact that these infections are rare and affect only high risk groups, the possibility of a false *B. anthracis* diagnosis due to infection by other bacilli from the *cereus* group is still theoretically possible. Therefore, in view of the fact that *B. anthracis* genome shares extensive sequence similarity to those of *B. cereus* and *B. thuringiensis*, the use of the biomarkers as diagnostic tools may be favored by their ability to discern between *B. anthracis* and these closely related species.

To determine the specificity of the three biomarkers identified in this study, the inventors conducted a sequence analysis of the genomes of *B. thuringiensis, B. cereus, B. licheniformis* and *B. subtilis* (the 2 later strains are more distant phyla yet, invoked in sporadic rare human infections, Blue et al., 1995; Zwick et al., 2008; Matsumoto et al., 2000), examining all the strains available in the NCBI data base. Annotated ORFs of 9 *Bacillus cereus*, 10 *Bacillus thuringiensis*, 4 *Bacillus licheniformis* and 12 *Bacillus subtilis* strain sequenced-genomes available in the NCBI data base at the time of this study, were examined for the presence of orthologues (exhibiting more than 80% identity across full sequence coverage [Expectation value E$\delta$e$^{-10}$]).

None of the three biomarkers have orthologs in the genomes of the *B. licheniformis* and *B. subtilis* strains scrutinized. For example, the homologues (functional equivalents) of NlpC/P60-family endopeptidase and HtrA in *B. licheniformis* exhibit only 50% and 44%, respectively, identity with the genes of *B. anthracis*. Similarly, the identity exhibited by the *B. subtilis* homologues is lower than 50%. The protein BA0796 is unique to the *cereus* group (which comprises *B. anthracis, B. cereus* and *B. thuringiensis*). The genomes of the closely related *B. cereus* and *B. thuringiensis* strains, do exhibit orthologues of the three biomarkers, yet judicious data mining of studies involving the related strains revealed that none of the novel markers were detected in their secretomes (Gohar et al., 2002, 2005 and 2008; DelVecchio et al., 2006; Voigt et al., 2004, 2006, 2008). Furthermore, the uniqueness of the three biomarkers to *B. anthracis* was confirmed by direct examination (by Western blot analysis) of the secretomes of *B. cereus, B. thuringiensis* and *B. subtilis* and compared to that of *B. anthracis* (FIG. 4). Notably, the three biomarkers could be detected in significant amounts only in the *B. anthracis* culture and not in that of *B. cereus, B. thuringiensis* and *B. subtilis*. The inventors therefore concluded that the three biomarkers, exhibit high specificity for *B. anthracis* infection, facilitating their use in the development of diagnostic tools. Furthermore, it should be noted that *B. anthracis* can be easily discerned from the closely related *B. cereus* and *B. thuringiensis* by inspection of the hemolytic character of the respective colonies: while *B. thuringiensis* and *B. cereus* bacterial colonies are hemolytic (generate a characteristic cleared aura when plated on agar-blood bacteriological plates), those of *B. anthracis* are not.

REFERENCES

Ahmed, N. et al. (2003) *Proteomics* 3:1980-1987.
Antelmann, H. et al. (2005) *Proteomics* 5:3684-3695.
Altboum, Z. et al. (2002) *Infect Immun* 70: 6231-6241.
Ariel, N. et al. (2002) *Infect. Immun.* 7: 6817-6827.
Ariel, N. et al. (2003) *Infect. Immun.* 71: 4563-4579.
Bjorhall, K. et al. (2005) *Proteomics.* 5:307-3017.
Bryskier, A. (2002) *Clinical Microbiology and Infection* 8:467-478.
Cendrowski, S. et al. (2004) *Molec. Microbiol.* 551:407-417.
Chitlaru, T. et al. (2004) *Proteomics* 4: 677-691.
Chitlaru, T. et al. (2006) *J Bacteriol.* 188: 3551-3571.
Chitlaru, T. et al. (2007) *Infect Immun* 75: 2841-2852.
Cohen, S et al. (2000) *Infect Immun* 68: 4549-4558.
Delvecchio, V. G. et al. (2006) *Appl Environ. Microbiol.* 72:6355-6363.
Dal Molin, F. et al (2008) *Toxicon* 52:824-828.
Dinges, M., et al. (2000) *Clinical Microbiology Reviews.* 13:16-36.
Dixon, T. C. et al. (1999) *New Engl J. Med.* 341:815-826.
Echan, L. A. et al. (2005) *Proteomics* 5:3292-3303.
Edwards, K. A. et al. (2006) *Anal. Bioanal. Chem.* 384:73-84.
Ewalt. K. et al. (2001) *Anal Biochem.* 289:162-172.
Francis, A. W. et al. (2005) *Biochim. Biophyis. Acta* 1748: 191-200.
Gat, O. et al. (2003) *Infect Immun* 71: 801-813.
Gat, O. et al. (2005) *Mol Microbiol* 58: 533-551.
Gat, O. et al. (2006) *Infect Immun* 74: 3987-4001.

Gat, O. et al. (2007) In: *Methods in Molecular Biology*. Vol. 375. Grandi, G. (ed): In Vitro Transcription and Translation Protocols. Humana Press, Totowa, N.J. Chapter 11, pp. 211-233.
Gat, O. et al. (2008) *Mol Microbiol.* 70:983-999.
Gohar, M. et al. (2002) *Proteomics* 2:784-791.
Gohar, M. et al. (2005) *Proteomics*. 5:3696-3711.
Gohar M. et al. (2008) *PLOS ONE* 3(7):e2793. www.plosone.org.
Govorukhina, N. I. et al. (2003) *J. Chromatogr. A.* 1009: 171-178.
Grosfeld, H. et al. (2003) *Infect Immun* 71: 374-383.
Issaq H., Z. Xiao, and T. D. Veenstra. (2007) *Chem. Rev.* 107:3601-3620.
Kobiler, et al. (2006) *Infect. Immun.* 74: 5871-5876.
Lacy, T. M., and R. J. Collier. (2002) *Microbiol. Immunol.* 271: 62-85.
Leppla, S. (1999) The Bifactorial *B. anthracis* lethal and oedema toxins. In: *Comprehensive sourcebook of bacterial protein toxins*. Eds. J. E. Alouf and J. H. Freer. Academic Press. London, UK, 243-263.
Lim, D. et al. (2005) *Clinical Microbiology Reviews* 18:583-607.
Mendelson, I., et al. (2005) *Vaccine* 23: 5688-5697.
Peruski, A. H. et al. (2002) *J. Immunol. Methods* 263:35-41.
Reuveny, S. et al. (2002) *Infection and Immunity.* 69:2888-2893.
Righetti, P. G. et al. (2006) *Proteomics* 6:3980-3992.
Rivera V. R. et al. (2006) *Anal Biochem.* 353:248-56.
Rossi, C. A. et al. (2008) *Infect. Immun.* 76:5790-5801.
Shafazand, S. et al. (1999) *Chest.* 116:1369-1376.
Stern E. J. et al. (2008) *Emerg. Infect. Dis.* 14:4. http://www2a.cdc.gov/EID/content/14/407-0969.htm
Turnbull, P. C. B. (1999) *Journal of Applied Microbiol.* 87:237-240.
Voigt, B. et al. (2004) *Proteomics* 4:1465-1490.
Voigt, B. et al. (2005) *Proteomics* 6: 268-281.
Voigt, B. et al. (2009) *J. Molec. Microbiol. Biotechnol.* 16:53-68.
Wang, Y. Y. et al. (2003) *Proteomics* 3:243-248.
Wu, H.-J. et al. (2008) *Current Opinion in Chemical Biology.* 12:93-101.

---

The invention claimed is:

1. A purified antibody or a fragment thereof that specifically binds to the early stage *Bacillus anthracis* infection biomarker, HtrA BA3660 protein, consisting of the amino acid sequence of SEQ ID NO: 1 or a specific epitope thereof.

2. The purified antibody of claim 1, wherein the purified antibody is produced by a method comprising immunizing an animal by:
   (a) DNA vaccination with a vector comprising a purified DNA sequence encoding the amino acid sequence of SEQ ID NO: 1; or
   (b) injection of a purified polypeptide comprising the amino acid sequence as set forth in SEQ ID NO: 1.

3. A composition comprising at least one purified antibody or a fragment thereof that specifically binds to the early stage *Bacillus anthracis* infection biomarker protein, HtrA BA3660, wherein the HtrA BA3660 consists of the amino acid sequence of SEQ ID NO: 1 or a specific epitope thereof.

4. The composition of claim 3, wherein the at least one purified antibody is produced by a method comprising immunizing an animal by:
   (a) DNA vaccination with a vector comprising an purified DNA sequence encoding the amino acid sequence of SEQ ID NO: 1; or
   (b) injection of a purified polypeptide comprising the amino acid sequence as set forth in SEQ ID NO: 1.

5. A kit comprising:
   (a) at least one purified antibody or a fragment thereof that specifically binds to the early stage *Bacillus anthracis* infection biomarker protein, HtrA BA3660, wherein the HtrA BA3660 consists of the amino acid sequence of SEQ ID NO: 1 or a specific epitope thereof and
   (b) instructions for carrying out the detection of the presence of said biomarker in a body sample to be tested.

6. The kit of claim 5 further comprising at least one of:
   (a) at least a means for collecting the body sample to be tested;
   (b) at least one compartment containing the at least one purified antibody;
   (c) at least one secondary antibody for the recognition of the at least one purified antibody;
   (d) at least one assay reagent that enables the detection of the at least one secondary antibody; and
   (e) at least one control sample.

7. The kit of claim 5, wherein the at least one purified antibody is a purified polyclonal antibody.

8. The kit of claim 5, wherein the at least one purified antibody is a purified monoclonal antibody.

9. A method for the diagnosis of *Bacillus anthracis* early stage infection in a mammalian subject, said method comprising the steps of:
- (a) obtaining a body sample from said subject;
- (b) providing at least one purified antibody or the fragment thereof that specifically binds to the early stage *Bacillus anthracis* infection biomarker, HtrA BA3660 protein, consisting of the amino acid sequence of SEQ ID NO: 1 or a specific epitope thereof;
- (c) contacting an aliquot of said body sample with said at least one purified antibody or the fragment thereof; and
- (d) determining the presence or the absence of the early stage *Bacillus anthracis* infection biomarker HtrA BA3660 protein in said body sample;
- whereby the presence of said early stage *Bacillus anthracis* infection biomarker HtrA BA3660 protein in said body sample indicates that said subject has the early stage *Bacillus anthracis* infection.

* * * * *

SEQUENCE LISTING

```
<160> NUMBER OF SEQ ID NOS: 3

<210> SEQ ID NO 1
<211> LENGTH: 413
<212> TYPE: PRT
<213> ORGANISM: Bacillus anthracis

<400> SEQUENCE: 1

Met Gly Tyr Tyr Asp Gly Pro Asn Leu Asn Glu Glu His Ser Glu Thr
1               5                   10                  15

Arg Glu Val Arg Lys Ser Gly Ser Lys Lys Gly Tyr Phe Phe Thr Gly
            20                  25                  30

Leu Val Gly Ala Val Val Gly Ala Val Ser Ile Ser Phe Ala Ala Pro
        35                  40                  45

Tyr Met Pro Trp Ala Gln Asn Asn Gly Ala Thr Val Ser Ser Phe Ser
    50                  55                  60

Ser Asp Ser Lys Val Glu Gly Thr Val Val Pro Val Val Asn Lys Ala
65                  70                  75                  80

Lys Asn Glu Thr Asp Leu Pro Gly Met Ile Glu Gly Ala Lys Asp Val
            85                  90                  95

Val Val Gly Val Ile Asn Met Gln Gln Ser Ile Asp Pro Phe Ala Met
        100                 105                 110

Gln Pro Thr Gly Gln Glu Gln Gln Ala Gly Ser Gly Ser Gly Val Ile
    115                 120                 125

Tyr Lys Lys Ala Gly Asn Lys Ala Tyr Ile Val Thr Asn Asn His Val
    130                 135                 140

Val Asp Gly Ala Asn Lys Leu Ala Val Lys Leu Ser Asp Gly Lys Lys
145                 150                 155                 160

Val Asp Ala Lys Leu Val Gly Lys Asp Pro Trp Leu Asp Leu Ala Val
            165                 170                 175

Val Glu Ile Asp Gly Ala Asn Val Asn Lys Val Ala Thr Leu Gly Asp
        180                 185                 190

Ser Ser Lys Ile Arg Ala Gly Glu Lys Ala Ile Ala Ile Gly Asn Pro
    195                 200                 205

Leu Gly Phe Asp Gly Ser Val Thr Glu Gly Ile Ile Ser Ser Lys Glu
```

```
        210                 215                 220
Arg Glu Ile Pro Val Asp Ile Asp Gly Asp Lys Arg Ala Asp Trp Asn
225                 230                 235                 240

Ala Gln Val Ile Gln Thr Asp Ala Ala Ile Asn Pro Gly Asn Ser Gly
                245                 250                 255

Gly Ala Leu Phe Asn Gln Asn Gly Glu Ile Ile Gly Ile Asn Ser Ser
                260                 265                 270

Lys Ile Ala Gln Gln Glu Val Glu Gly Ile Gly Phe Ala Ile Pro Ile
                275                 280                 285

Asn Ile Ala Lys Pro Val Ile Glu Ser Leu Glu Lys Asp Gly Val Val
                290                 295                 300

Lys Arg Pro Ala Leu Gly Val Gly Val Val Ser Leu Glu Asp Val Gln
305                 310                 315                 320

Ala Tyr Ala Val Asn Gln Leu Lys Val Pro Lys Glu Val Thr Asn Gly
                325                 330                 335

Val Val Leu Gly Lys Ile Tyr Pro Ile Ser Pro Ala Glu Lys Ala Gly
                340                 345                 350

Leu Glu Gln Tyr Asp Ile Val Val Ala Leu Asp Asn Gln Lys Val Glu
                355                 360                 365

Asn Ser Leu Gln Phe Arg Lys Tyr Leu Tyr Glu Lys Lys Val Gly
                370                 375                 380

Glu Lys Val Glu Val Thr Phe Tyr Arg Asn Gly Gln Lys Met Thr Lys
385                 390                 395                 400

Thr Ala Thr Leu Ala Asp Asn Ser Ala Thr Lys Asn Gln
                405                 410

<210> SEQ ID NO 2
<211> LENGTH: 420
<212> TYPE: PRT
<213> ORGANISM: Bacillus anthracis

<400> SEQUENCE: 2

Met Lys Lys Val Ile Ala Gly Leu Ala Ala Ala Ser Val Val Gly Val
1               5                   10                  15

Ala Val Pro Gly Met Asp Ser Ala Gln Ala Gln Val Ser Asn Glu Ala
                20                  25                  30

Leu Lys Glu Ile Asn Gly Gln Ala Gln Thr Gln Thr Thr Val Thr Glu
            35                  40                  45

Thr Lys Thr Val Glu Thr Lys Ser Asp Leu Lys Tyr Thr Val Thr Ala
        50                  55                  60

Asp Val Leu Asn Val Arg Ser Gly Ala Gly Thr Gly His Ser Val Ile
65                  70                  75                  80

Ser Lys Val Lys Gln Gly Gln Val Leu Gln Val Ile Gly Gln Glu Asn
                85                  90                  95

Gly Trp Phe Lys Val Thr Val Asn Gly Gln Thr Gly Tyr Val Ser Gly
                100                 105                 110

Asp Phe Val Thr Thr Gly Gly Lys Thr Gly Thr Thr Val Gln Gln Gly
                115                 120                 125

Thr Gly Thr Tyr Thr Val Asn Val Ser Ser Leu Asn Val Arg Thr Gly
                130                 135                 140

Pro Ser Thr Ser His Thr Val Leu Gly Ser Val Asn Lys Gly Lys Thr
145                 150                 155                 160

Val Gln Val Val Ser Glu Val Gln Asp Trp Phe Lys Ile Asn Phe Asn
                165                 170                 175

Gly Gly Thr Gly Tyr Val Ser Lys Asp Phe Val Thr Lys Gly Gly Ser
```

```
                    180             185              190
Ala Val Ser Asn Gln Thr Gln Gln Pro Thr Thr Asn Asn Thr Thr
            195                 200             205

Thr Val Gln Thr Gly Gly Ser Tyr Val Val Asn Thr Gly Ala Leu Lys
            210             215                 220

Val Arg Thr Gly Pro Ala Thr Tyr Asn Ala Val Ile Gly Gly Val Thr
225             230                 235                 240

Asn Gly Thr Val Leu Asn Val Thr Gly Ala Glu Asn Gly Trp Tyr Lys
                245                 250                 255

Ile Asn His Asn Gly Arg Thr Gly His Val Ser Ala Asp Phe Val Lys
            260                 265                 270

Phe Val Lys Gly Gly Val Asn Asn Val Thr Asn Asn Val Gln Gln Pro
            275                 280                 285

Val Lys Asp Val Gln Lys Pro Thr Thr Gly Gly Asn Thr Ser Ser Ile
            290                 295                 300

Ala Gly Phe Ala Arg Ser Leu Asn Gly Ser Pro Tyr Arg Thr Ala Gly
305             310                 315                 320

Thr Thr Pro Ala Gly Phe Asp Cys Ser Gly Phe Ile His Tyr Val Leu
                325                 330                 335

Asn Gln Thr Gly His Lys Gly Ala Arg Gln Thr Val Ala Gly Tyr Trp
                340                 345                 350

Ser Ser Lys Thr Lys Thr Ser Asn Pro Gln Pro Gly Asp Leu Val Tyr
            355                 360                 365

Phe Gln Asn Thr Tyr Lys Ser Gly Pro Ser His Met Gly Val Tyr Leu
            370                 375                 380

Gly Asn Gly Gln Phe Ile Ser Ala Glu Thr Asp Ala Thr Gly Val Arg
385                 390                 395                 400

Ile Ser Ser Val Ser Asn Ser Tyr Trp Ser Lys His Leu Leu Gly Tyr
                405                 410                 415

Thr Lys Ala Tyr
            420

<210> SEQ ID NO 3
<211> LENGTH: 386
<212> TYPE: PRT
<213> ORGANISM: Bacillus anthracis

<400> SEQUENCE: 3

Met Lys Lys Phe Met Gly Ile Ala Thr Ala Ala Val Phe Gly Leu Gly
1               5                   10                  15

Ile Phe Thr Thr Ser Ala Lys Ala Glu Thr Ile Val Thr Thr Asp Val
            20                  25                  30

Leu Asn Val Arg Glu Asn Pro Thr Thr Glu Ser Lys Val Gly Lys
            35                  40                  45

Leu Leu Asp Gly Tyr Lys Val Asn Val Leu His Thr Glu Asn Gly Trp
        50                  55                  60

Ser Lys Val Lys Leu Asn Ser Gly Lys Glu Ala Phe Ile Ser Ala Asp
65                  70                  75                  80

Tyr Thr Lys Asp Thr Tyr Tyr Val Thr Ala Asn Val Leu Asn Val Arg
                85                  90                  95

Ala Gly Ala Asn Thr Asp Ser Glu Ile Leu Gly Lys Leu Lys Gln Asp
            100                 105                 110

Asp Val Ile Glu Thr Thr His Gln Val Glu Asn Gly Trp Ile Gln Phe
        115                 120                 125

Glu Tyr Asn Gly Lys Thr Ala Tyr Val His Val Pro Tyr Leu Thr Gly
```

-continued

```
            130                 135                 140
Lys Ala Pro Val Lys Val Gln Pro Val Val Lys Ala Glu Lys Thr Thr
145                 150                 155                 160

Thr Val Gln Asp Thr Ala Lys Ala Val Ala Thr Thr Lys Ala Arg Glu
                165                 170                 175

Val Ala Glu Thr Gln Ala Lys Ala Lys Ala Glu Glu Ala Thr Lys Ala
                180                 185                 190

Arg Glu Val Ala Glu Ala Gln Ala Ala Ala Lys Ala Arg Glu Ala Ala
                195                 200                 205

Lys Ala Gln Glu Ala Ala Lys Ala Gln Ala Glu Ala Lys Ala Gln Glu
210                 215                 220

Ala Ala Glu Ala Gln Ala Ala Lys Ala Gln Glu Ala Ala Lys Ala
225                 230                 235                 240

Arg Glu Ala Ala Lys Ala Gln Ala Glu Ala Lys Ala Gln Glu Ala Ala
                245                 250                 255

Glu Ala Arg Glu Ala Ala Lys Ala Gln Lys Pro Ala Thr Gln Gln Pro
                260                 265                 270

Val Ala Lys Glu Thr Glu Thr Ser Ala Pro Ser Ser Ser Arg Glu Leu
                275                 280                 285

Arg Val Val Ala Thr Ala Tyr Thr Ala Asp Pro Leu Glu Asn Gly Tyr
                290                 295                 300

Lys Ala Gly Asp Gln Val Lys Ser Ala Leu Gly His Asn Leu Thr Ala
305                 310                 315                 320

Asn Pro Asn Met Lys Leu Ile Ala Val Asp Pro Ser Val Ile Pro Leu
                325                 330                 335

Gly Ser Lys Val Trp Val Glu Gly Tyr Gly Val Ala Ile Ala Gly Asp
                340                 345                 350

Thr Gly Gly Ala Ile Lys Gly Asn Lys Ile Asp Val Leu Met Pro Asp
                355                 360                 365

Lys Gly Thr Ser Ser Asn Trp Gly Arg Lys Thr Val Thr Val Lys Val
                370                 375                 380

Leu Asn
385
```